United States Patent [19]
Miller et al.

[11] Patent Number: 5,889,024
[45] Date of Patent: Mar. 30, 1999

[54] SUBSTITUTED HETEROCYCLES

[75] Inventors: Scott C. Miller, Hamden, Conn.; Robert T. Jacobs; Ashokkumar B. Shenvi, both of Wilmington, Del.

[73] Assignee: Zeneca Limited, London, United Kingdom

[21] Appl. No.: 635,161

[22] Filed: Apr. 23, 1996

[30] Foreign Application Priority Data

Apr. 29, 1995 [GB] United Kingdom ............... 9508786

[51] Int. Cl.⁶ ............... A61K 31/445; C07D 211/00
[52] U.S. Cl. ............... 514/326; 546/186; 546/187; 514/316; 514/317
[58] Field of Search ............... 546/187; 514/326

[56] References Cited

U.S. PATENT DOCUMENTS

| | | |
|---|---|---|
| 4,782,061 | 11/1988 | Kruse et al. |
| 5,236,921 | 8/1993 | Emonds-Alt et al. |
| 5,300,648 | 4/1994 | Emonds-Alt et al. |
| 5,340,822 | 8/1994 | Emonds-Alt et al. |
| 5,411,971 | 5/1995 | Emonds-Alt et al. |
| 5,434,158 | 7/1995 | Shah . |

FOREIGN PATENT DOCUMENTS

| | | |
|---|---|---|
| 2029275 | 5/1991 | Canada . |
| 2067924 | 11/1992 | Canada . |
| 2090785 | 9/1993 | Canada . |
| 0190472 | 8/1986 | European Pat. Off. . |
| 0428434 | 5/1991 | European Pat. Off. . |
| 0474561 | 3/1992 | European Pat. Off. . |
| 0512901 | 11/1992 | European Pat. Off. . |
| 0512902 | 11/1992 | European Pat. Off. . |
| 0515240 | 11/1992 | European Pat. Off. . |
| 0559538 | 9/1993 | European Pat. Off. . |
| 0625509 | 11/1994 | European Pat. Off. . |
| 0630887 | 12/1994 | European Pat. Off. . |
| 0680962 | 11/1995 | European Pat. Off. . |
| 923177 | of 0000 | South Africa . |
| 923178 | 1/1993 | South Africa . |
| 2248449 | 4/1992 | United Kingdom . |
| WO 94/10146 | 5/1994 | WIPO . |
| WO 94/29309 | 12/1994 | WIPO . |
| WO 95/05377 | 2/1995 | WIPO . |
| WO 95/12577 | 5/1995 | WIPO . |
| WO 95/15961 | 6/1995 | WIPO . |
| WO 95/16682 | 6/1995 | WIPO . |

OTHER PUBLICATIONS

A. Graham et al., "Isolation and Characterisation of the Human Lung NK–2 Receptor Gene Using Rapid Amplification of cDNA Ends", *Biochemical and Biophysical Research Communications*, (1991), vol. 177, No. 1, 8–16.

X. Emonds–Alt et al., "Pharmacological Profile and Chemical Synthesis of SR48968, a Non–Peptide Antagonist of the Neurokinin A ($NK_2$) Receptor", *Bioorganic & Medicinal Chemistry Letters*, (1993), vol. 3, No. 5, 925–930.

D. Aharony et al., "Pharmacologic Characterization of the Novel Ligand [4,5-³H–LEU⁹] Neurokinin–A Binding to NK–2 Receptors on Hamster Urinary Bladder Membranes", *Neuropeptides*, (1992), 23, 121–130.

M. Needham et al., "LCR/MEL: A Versatile System for High–Level Expression of Heterologous Proteins in Erthyroid Cells", *Nucleic Acids Research*, (1992), vol. 20, No. 5, 997–1003.

*Primary Examiner*—Jose'G. Dees
*Assistant Examiner*—Sabiha N. Qazi

[57] ABSTRACT

Compounds of formula I

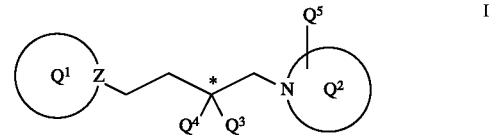

wherein $Q^1$, $Q^2$, $Q^3$, $Q^4$ and $Q^5$ have any of the meanings given in the specification, their N-oxides, and their pharmacuetically acceptable salts are nonpeptide antagonists NKA, useful for the treatment of asthma, etc. Also disclosed are pharmaceutical compositions, processes for preparing the compounds of formula I and intermediates.

6 Claims, No Drawings

SUBSTITUTED HETEROCYCLES

This invention concerns novel heterocyclic compounds which antagonize the pharmacological actions of one of the endogenous neuropeptide tachykinins known as neurokinins, particularly at the neurokinin 2 (NK2) receptor. The novel heterocyclic compounds are useful whenever such antagonism is desired. Thus, such compounds may be of value in the treatment of those diseases in which an NK2 receptor is implicated, for example, in the treatment of asthma and related conditions. The invention also provides pharmaceutical compositions containing the novel heterocyclic compounds for use in such treatment, methods for their use, and processes and intermediates for the manufacture of the novel heterocyclic compounds.

The mammalian neurokinins comprise a class of peptide neurotransmitters which are found in the peripheral and central nervous systems. The three principal neurokinins are Substance P (SP), Neurokinin A (NKA) and Neurokinin B (NKB). There are also N-terminally extended forms of at least NKA. At least three receptor types are known for the three principal neurokinins. Based upon their relative selectivities favoring the neurokinin agonists SP, NKA and NKB, respectively, the receptors are classifed as neurokinin 1 (NK1), neurokinin 2 (NK2) and neurokinin 3 (NK3) receptors, respectively. In the periphery, SP and NKA are localized in C-afferent sensory neurons, which neurons are characterized by non-myelinated nerve endings known as C-fibers, and are released by selective depolarization of these neurons, or selective stimulation of the C-fibers. C-Fibers are located in the airway epithelium, and the tachykinins are known to cause profound effects which clearly parallel many of the symptoms observed in asthmatics. The effects of release or introduction of tachykinins in mammalian airways include bronchoconstriction, increased microvascular permeability, vasodilation and activation of mast cells. Thus, the tachykinins are implicated in the pathophysiology and the airway hyperresponsiveness observed in asthmatics; and blockade of the action of released tachykinins may be useful in the treatment of asthma and related conditions. Peptidic NK2 antagonists have been reported. For example, a cyclic hexapeptide known as L-659,877 has been reported as a selective NK2 antagonist. Nonpeptidic tachykinin antagonists have been reported, for example in European Patent Application, Publication Number (EPA) 428434, EPA 474561, EPA 512901, EPA 512902, EPA 515240 and EPA 559538, as well as in WO 94/10146, EPA 0625509, EPA 0630887, WO 95/05377, WO 95/12577, WO 95/15961, EPA 680962, and WO 95/16682. We have discovered a series of nonpeptidic NK2 antagonists, and this is the basis for our invention.

According to the invention, there is provided a Compound of the invention which is a compound of formula I (formula set out hereinbelow following the Examples, together with other formulae denoted by Roman numerals) wherein $Q^1$ is a radical (attached at Z) selected from the group of radicals of formulae Ia, Ib, Ic, Id, Ie, If, Ig, Ih, Ij, Ik and Im, wherein for a radical of formula Ia, $z^a$ is nitrogen or a group $CR^{ad}$ in which $R^{ad}$ is hydrogen or $R^{ad}$ together with $R^{ac}$ and the existing carbon to carbon bond forms a double bond; $R^{aa}$ is Ar or Het; $R^{ab}$ is hydrogen and $R^{ac}$ is hydrogen or hydroxy or $R^{ac}$ together with $R^{ad}$ and the existing carbon to carbon bond forms a double bond, or $R^{ac}$ and $R^{ad}$ together form a diradical $—(CH_2)_j—$ in which j is an integer from 1 to 5; or $R^{ab}$ and $R^{ac}$ together form a diradical $—(CH_2)_k—$ in which k is an integer from 2 to 6, or $R^{ab}$ and $R^{ac}$ together are oxo or dialkylaminoalkyloxyimino of formula $=N—O—(CH_2)_q—NR^{ae}R^{af}$ in which q is the integer 2 or 3 and $R^{ae}$ and $R^{af}$ are independently hydrogen or (1–4C)alkyl, or the radical $NR^{ae}R^{af}$ is pyrrolidino, piperidino or morpholino;

for a radical of formula Ib, $Z^b$ is a substituted imino group $R^{ba}N$ or $R^{ba}CH_2N$ in which $R^{ba}$ is (3–7C)cycloakyl, Ar or Het; or $Z^b$ is a disubstituted methylene group $R^{bb}(CH_2)_p—C—R^{bc}$ in which $R^{bb}$ is Ar or Het; p is the integer 0 or 1; and $R^{bc}$ is hydrogen, hydroxy, (1–4C)alkoxy, (1–4C)alkanoyloxy, $COOR^{bd}$ (wherein $R^{bd}$ is hydrogen or (1–3C)alkyl), cyano, $NR^{be}R^{bf}$ or $SR^{bg}$ in which $R^{be}$ and $R^{bf}$ are independently hydrogen, (1–4C)alkyl, (1–4C)hydroxyalkyl or (1–4C)alkanoyl, or the radical $NR^{be}R^{bf}$ is pyrrolidino, piperidino or morpholino; and $R^{bg}$ is hydrogen or (1–4C)alkyl; or $R^{bc}$ forms a double bond with the carbon atom to which it is bonded and with the adjacent carbon atom in the piperidine ring;

for a radical of formula Ic, $R^{ca}$ is Ar or Het; and $Z^c$ is oxo, thio, sulfinyl, sulfonyl or imino of formula $—NR^{cb}—$ in which $R^{cb}$ is (1–3C)alkyl or $R^{cc}R^{cd}N—(CH_2)_q—$ in which q is the integer 2 or 3 and in which $R^{cc}$ and $R^{cd}$ are independently hydrogen or (1–3C)alkyl or the radical $R^{cc}R^{cd}N$ is pyrrolidino, piperidino or morpholino;

for a radical of formula Id, $R^{da}$ is hydrogen, (1–6C)alkyl, Ar, Het, α-hydroxybenzyl, styryl, or $R^{db}—$(1–3C)alkyl in which $R^{db}$ is aryl, pyridyl, pyridylthio or 1-methyl-2-imidazolylthio in which an aromatic group or portion of $R^{da}$ may bear one or more halo, hydroxy, (1–4C)alkyl or (1–4C)alkoxy substituents; $X_d$ is oxy or $—CHR^{dc}—$; $R^{dc}$ is hydrogen, hydroxy, (1–3C)alkoxy, (1–4C)alkanoyloxy, $NR^{dd}R^{de}$ or (1–4C)alkanoylarino; $R^{dd}$ and $R^{de}$ are independently hydrogen or (1–4C)alkyl or the radical $NR^{dd}R^{de}$ is pyrrolidino, piperidino or morpholino; p is the integer 0 or 1; and $Z^d$ is a single bond (except when $R^{da}$ is hydrogen or p is 1), methylene or carbonyl;

for a radical of formula Ie, $J^e$ is oxygen, sulfur or $NR^{ea}$ in which $R^{ea}$ is hydrogen or (1–3C)alkyl; $R^{eb}$ is hydrogen, (1–6C)alkyl which may bear a hydroxy substituent and/or one to three fluoro substituents, (3–6C)alkenyl (in which a vinyl carbon is not bound to nitrogen), 2-hydroxyethyl, (3–7C)cyloalkyl, Ar or Het; $R^{ec}$ is hydrogen, (1–6C)alkyl which may bear a hydroxy substituent and/or one to three fluoro substituents, (3–6C)cycloalkyl, (1–5C)alkoxy (only when $J^e$ is oxygen), (3–6C)cycloalkoxy (only when $J^e$ is oxygen), or an amino group of formula $NR^{ed}R^{ee}$ containing zero to seven carbon atoms in which each of $R^{ed}$ and $R^{ee}$ is independently hydrogen, (1–5C)alkyl or (3–6C)cycloalkyl, or the radical $NR^{ed}R^{ee}$ is pyrrolidino, piperidino, morpholino, thiomorpholino (or its S-oxide) or piperazinyl (which piperazinyl group may bear a (1–3C)alkyl substituent at the 4-position);

for a radical of formula If, $J^f$ is oxygen, sulfur or $NR^{fa}$ in which $R^{fa}$ is hydrogen or (1–3C)alkyl; $L^f$ is a divalent hydrocarbon group in which the 1-position is bound to the carbon bearing the group $J^f$, the divalent group $L^f$ being selected from trimethylene, cis-propenylene, tetramethylene, cis-butenylene, cis-but-3-enylene, cis,cis-butadienylene, pentamethylene and cis-pentenylene which divalent group $L^f$ itself may bear one or two methyl substituents;

for a radical of formula Ig, $Z^g$ is (1–8C)alkyl or (3–8C)cycloalkyl which may bear one or more substituents selected from the group consisting of halo, (3–6C)cycloalkyl, cyano, nitro, hydroxy, (1–4C) alkoxy, (1–5C)alkanoyloxy, aroyl, heteroaroyl, oxo, imino (which may bear a (1–6C)alkyl, (3–6C) cycloalkyl, (1–5C)alkanoyl or aroyl substituent), hydroxyimino (which hydroxyimino may bear a (1–4C)alkyl or a phenyl substituent on the oxygen), an amino group of formula $NR^{ga}R^{gb}$, an amino group of formula $NR^{gc}R^{gd}$, an amnidino group of formula $C(=NR^{gg})NR^{ge}R^{gf}$, and a carbamoyl group of formula $CON(OR^{gh})R^{gi}$, but excluding any radical wherein a hydroxy and an oxo substituent together form a carboxy group, wherein an amino group of formula $NR^{ga}R^{gb}$ contains zero to seven carbon atoms and each of $R^{ga}$ and $R^{gb}$ is independently hydrogen, (1–5C)alkyl or (3–6C)cycloalkyl, or the radical $NR^{ga}R^{gb}$ is pyrrolidino, piperidino, morpholino, thiomorpholino (or its S-oxide) or piperazinyl (which piperazinyl may bear a (1–3C)alkyl substituent group at the 4-position); and wherein $R^{gc}$ is hydrogen or (1–3C)alkyl and $R^{gd}$ is (1–5C) alkanoyl, aroyl or heteroaroyl; or $R^{gd}$ is a group of formula $C(=J^g)NR^{ge}R^{gf}$ in which $J^g$ is oxygen, sulfur, $NR^{gg}$ or $CHR^{gj}$; and wherein the amino group $NR^{ge}R^{gf}$ contains zero to seven carbon atoms and each of $R^{ge}$ and $R^{gf}$ is independently hydrogen, (1–5C)alkyl or (3–6C)cycloalkyl, or the radical $NR^{ge}R^{gf}$ is pyrrolidino, piperidino, morpholino, thiomorpholino (or its S-oxide) or piperazinyl (which piperazinyl may bear a (1–3C)alkyl substituent at the 4-position) or $R^{ge}$ is hydrogen or (1–4C)alkyl and $R^{gf}$ together with $R^{gg}$ forms an ethylene or trimethylene group; $R^{gg}$ is hydrogen, (1–4C)alkyl or together with $R^{gf}$ forms an ethylene or trimethylene group; $R^{gj}$ is cyano, nitro or $SO_2R^{gk}$ and $R^{gk}$ is (1–4C)alkyl or phenyl; $R^{gh}$ and $R^{gi}$ are independently (1–3C)alkyl; and in which a cyclic group which is a substituent on $Z^g$ or formed by substitution on $Z^g$ may bear one or more (1–3C)alkyl groups on carbon as further substituents; and in which any aryl or heteroaryl group which is a part of the group $Z^g$ may bear one or more halo, (1–4C)alkyl, (1–4C) alkoxy, cyano, trifluoromethyl or nitro substituents;

for a radical of formula Ih, $G^h$ denotes a single bond, a double bond or a divalent hydrocarbon radical; $J^h$ denotes a radical joined to the ring by a single bond if $G^h$ denotes a double bond or, otherwise, a radical joined by a double bond; $M^h$ denotes a heteroatom a substituted heteroatom, or a single bond; and $L^h$ denotes a hydrocarbon radical in which the 1-position is attached to $M^h$; wherein the values of $G^h$, $J^h$, $M^h$ and $L^h$ are selected from (a) $G^h$ is a single bond; $J^h$ is oxo or thioxo; $M^h$ is oxy, thio or $NR^{ha}$; and $L^h$ is $L^{ha}$;
(b) $G^h$ is a single bond; $J^h$ is $NR^{hb}$; $M^h$ is $NR^{ha}$; and $L^h$ is $L^{ha}$;
(c) $G^h$ is a double bond, $J^h$ is $OR^{ha}$, $SR^{ha}$ or $NR^{hc}R^{hd}$; $M^h$ is nitrogen; and $L^h$ is $L^{ha}$;
(d) $G^h$ is methylene which may bear one or two methyl substituents; $J^h$ is oxo, thio or $NR^{he}$; $M^h$ is oxy, thio, sulfinyl, sulfonyl or $NR^{ha}$; and $L^h$ is $L^{hb}$;
(e) $G^h$ is a single bond; $J^h$ is oxo, thioxo or $NR^{he}$; $M^h$ is nitrogen; and $L^h$ is $L^{hc}$;
(f) $G^h$ is methine, which may bear a (1–3C)alkyl substituent; $J^h$ is oxo, thioxo or $NR^{he}$; $M^h$ is nitrogen; and $L^h$ is $L^{hd}$; (g) $G^h$ is cis-vinylene, which may bear one or two methyl substituents; $J^h$ is oxo, thioxo, or $NR^{he}$; $M^h$ is nitrogen; and $L^h$ is $L^{he}$; and
(h) $G^h$ is a single bond; $J^h$ is oxo or thioxo; $M^h$ is a single bond; and $L^h$ is $L^{hf}$;

wherein $R^{ha}$ hydrogen or (1–3C)alkyl; $R^{hb}$ is hydrogen, (1–3C)alkyl, cyano, (1–3C)alkylsulfonyl or nitro; $R^{hc}$ and $R^{hd}$ are independently hydrogen or (1–3C)alkyl or the radical $NR^{hc}R^{bd}$ is pyrrolidino, piperidino, morpholino, thiomorpholino (or its S-oxide) or piperazinyl (which piperazinyl may bear a (1–3C)alkyl substituent at the 4-position); $R^{he}$ is hydrogen or (1–3C) alkyl; $L^{ha}$ is ethylene, cis-vinylene, trimethylene or tetramethylene which radical $L^{ha}$ itself may bear one or two methyl substituents; $L^{hb}$ is ethylene or trimethylene which radical $L^{hb}$ itself may bear one or two methyl substituents; $L^{hc}$ is prop-2-en-1-yliden-3-yl, which radical $L^{hc}$ itself may bear one or two methyl substituents; $L^{hd}$ is cis-vinylene, which radical $L^{hd}$ itself may bear one or two methyl substituents; $L^{he}$ is methine, which radical $L^{he}$ itself may bear a (1–3C)alkyl substituent; and $L^{hf}$ is 4-oxabutan-1,4-diyl;

for a radical of formula Ij, $X^j$ is (1–6C)alkyl, $-CH_2OR^{ja}$, $-CH_2SR^{ja}$, $-CH_2S(O)R^{jg}$, $-CH_2S(O)_2R^{jg}$, $-COR^{ja}$, $-COOR^{ja}$, $-C(=J^{ja})NR^{jb}R^{jc}$, $-C(R^{ja})(OR^{jd})(OR^{je})$, $-CH_2N(R^{ja})C(=J^{ja})R^{jf}$, $-CH_2N(R^{ja})COOR^{jg}$ or $-CH_2N(R^{ja})C(=J^{ja})NR^{jb}R^{jc}$; $B^j$ is a direct bond and $L^j$ is a hydrocarbon chain in which the 1-position is bound to $B^j$ and $L^j$ is selected from trimethylene, tetramethylene, cis-1-butenylene and cis,cis-butadienylene; or $B^j$ is $N(R^{jh})$ and $L^j$ is a hydrocarbon chain selected from ethylene, trimethylene and cis-vinylene; or $B^j$ is N and $L^j$ is a hydrocarbon chain in which the 1-position is bound to $B^j$ and $L^j$ is cis,cis-prop-2-en-1-ylidin-3-yl; $J^j$ and $j^{ja}$ are independently oxygen or sulfur; $R^{ja}$, $R^{jf}$ and $R^{jh}$ are independently hydrogen or (1–6C)alkyl; $R^{jb}$ and $R^{jc}$ are independently hydrogen or (1–6C)alkyl; or the radical $NR^{jb}R^{jc}$ is pyrrolidino, piperidino, morpholino, thiomorpholino (or its S-oxide) or piperazinyl (which piperazinyl may bear a (1–3C)alkyl substituent at the 4-position); $R^{jd}$ and $R^{je}$ are independently (1–3C)alkyl or together form a divalent hydrocarbon chain selected from ethylene and trimethylene; $R^{jg}$ is (1–6C)alkyl;

for a radical of formula Ik, $Z^k$ is a nitrogen linked radical of formula II wherein $E^1$, $E^2$, $E^3$ and $E^4$ form a divalent four membered chain ($-E^1=E^2-E^3=E^4-$) in which each of $E^1$, $E^2$, $E^3$ and $E^4$ is methine; or in which one or two of $E^1$, $E^2$, $E^3$ and $E^4$ is nitrogen and the remaining $E^1$, $E^2$, $E^3$ and $E^4$ are methine; and further wherein one or more of $E^1$, $E^2$, $E^3$ and $E^4$ which is methine may bear a halo, (1–3C)alkyl, hydroxy, (1–3C)alkoxy, (1–3C) alkylthio, (1–3C)alkylsulfinyl or (1–3C) alkylsulfonyl substituent; and wherein the radicals $F^k$, $G^k$ and $I^k(X^k)$ are selected from
(a) $G^k$ is a direct bond, $I^k(X^k)$ is a radical having the formula $=C(Z^k)-$ and $F^k$ is a radical selected from $-CH=$ and $-N=$;

(b) $G^k$ is a direct bond, $I^k(X^k)$ is a radical having the formula —C(=$J^k$)— and $F^k$ is a radical selected from —N($R^{kf}$)—, —CH$_2$—CH$_2$—, —CH=CH—, —CH$_2$—N($R^{kf}$)— and —CH=N—;

(c) $G^k$ is a radical having the formula —CH$_2$—, $I^k(X^k)$ is a radical having formula —C(=$J^k$)— and $F^k$ is selected from —CH$_2$— and —N($R^{kf}$)—; and (d) $G^k$ is selected from —CH$_2$—, —CH$_2$—CH$_2$—, —CH=CH— and —N=CH—, $I^k(X^k)$ is a radical having the formula —C(=$J^k$)— and $F^k$ is a direct bond; wherein $J^k$ is oxygen or sulfur; $Z^k$ is —$OR^{ka}$, —$SR^{ka}$, —$COR^{ka}$, —$COOR^{ka}$, —C(=$J^{ka}$)$NR^{kb}R^{kc}$ or —C($R^{ka}$)($OR^{kd}$)($OR^{ke}$); $J^{ka}$ is oxygen or sulfur; $R^{ka}$ and $R^{kf}$ are independently hydrogen or (1–6C)alkyl; $R^{kb}$ and $R^{kc}$ are independently hydrogen or (1–6C)alkyl; or the radical $NR^{kb}R^{kc}$ is pyrrolidino, piperidino, morpholino, thiomorpholino (or its S-oxide) or piperazinyl (which piperazinyl may bear a (1–3C)alkyl substituent at the 4-position); $R^{kd}$ and $R^{ke}$ are independently (1–3C)alkyl or $R^{kd}$ and $R^{ke}$ together form ethylene or trimethylene; or $Z^k$ is an imido radical selected from phthalimido, succinimido, maleimido, glutarimido, and 3-oxa-, 3-thia- and 3-azaglutarimido, in which the imido radical may bear one or more (1–3C) alkyl substituents and, in addition, the aromatic portion of the phthalimido may bear one or more halo, hydroxy or (1–3C)alkoxy substituents; and for a radical of formula Im, $R^{ma}$ and $R^{mb}$ are independantly selected from the group consisting of hydrogen, (1–3C)alkyl, benzyl, and phenethyl; and $R^{mc}$ is pyrrolidino, piperidino, morpholino, thiomorpholino (or its S-oxide) or piperazinyl (which piperazinyl may bear a (1–3C)alkyl substituent at the 4-position); and wherein for a radical $Q^1$, Ar is a phenyl radical or an ortho-fused bicyclic carbocyclic radical of nine of ten ring atoms in which at least one ring is aromatic, which radical Ar may be unsubstituted or may bear one or more substituents selected from halo, cyano, trifluoromethyl, (1–C)alkyl, (1–4C)alkoxy, methylenedioxy, hydroxy, mercapto, —S(O)$_n R^{xa}$, (1–5C)alkanoyl, (1–5C)alkanoyloxy, nitro, $NR^{xb}R^{xc}$, $NR^{xd}R^{xe}$, C(=$NR^{xf}$)$NR^{xg}R^{xh}$, $CONR^{xb}R^{xc}$ and $COOR^{xj}$ wherein n is the integer 0, 1, or 2; $R^{xa}$ is (1–6C)alkyl, (3–6C)cycloalkyl or phenyl (which phenyl may bear a halo, trifluoromethyl, (1–3C)alkyl or (1–3C)alkoxy substitutent); the radical $NR^{xb}R^{xc}$ contains zero to seven carbons and each of $R^{xb}$ and $R^{xc}$ is independently hydrogen, (1–5C)alkyl or (3–6C)cycloalkyl, or the radical $NR^{xb}R^{xc}$ is pyrrolidino, piperidino, morpholino, thiomorpholine (or its S-oxide) or piperazinyl (which piperazinyl may bear a (1–3C)alkyl substituent at the 4-position); and wherein $R^{xd}$ is hydrogen or (1–4C) alkyl and $R^{xe}$ is (1–5C)alkanoyl, benzoyl; or a group of formula C(=$J^x$)$NR^{xg}R^{xh}$ in which $J^x$ is oxygen, sulfur, $NR^{xf}$ or $CHR^{xi}$; $R^{xf}$ is hydrogen, (1–5C)alkyl or together with $R^{xg}$ forms an ethylene or trimethylene diradical, the radical $NR^{xg}R^{xh}$ contains zero to 7 carbons and each of $R^{xg}$ amd $R^{xh}$ is independently hydrogen, (1–5C)alkyl or (3–6C)cycloalkyl, or the radical $NR^{xg}R^{xh}$ is pyrrolidino, piperidino, morpholino, thiomorpholino (or its S-oxide) or piperazinyl (which piperazinyl may bear a (1–3C)alkyl substituent at the 4-position); or $R^{xg}$ together with $R^{xf}$ forms an ethylene or trimethylene diradical and $R^{xh}$ is hydrogen or (1–5C)alkyl; $R^{xi}$ is cyano, nitro, (1–5C)alkylsulfonyl or phenylsulfonyl; and $R^{xj}$ is hydrogen, (1–5C)alkyl or benzyl; and Het is a radical (or stable N-oxide thereof) attached via a ring carbon of a monocyclic aromatic ring containing five or six ring atoms consisting of carbon and one to four heteroatoms selected from oxygen, sulfur and nitrogen, or an ortho-fused bicyclic heterocycle derived therefrom by fusing a propenylene, trimethylene, tetramethylene or benz-diradical, which radical Het may be unsubstituted or may be substituted on carbon by one or more of the substituents defined above for Ar and may be substituted on nitrogen by (1–3C)alkyl;

$Q^2$ is a nitrogen-linked five-membered aromatic ring containing 1–4 nitrogens, which is substituted at a ring position adjacent to the nitrogen-link by a group $Q^5$;

$Q^3$ is hydrogen or (1–3C)alkyl;

$Q^4$ is phenyl which may bear one or two substituents independently selected from halo, trifluoromethyl, hydroxy, (1–3C)alkoxy, (1–3C)alkyl and methylenedioxy; or $Q^4$ is thienyl, imidazolyl, benzo[b]thiophenyl or naphthyl any of which may bear a halo substituent; or $Q^4$ is biphenylyl; or $Q^4$ is carbon-linked indolyl which may bear a benzyl substituent at the 1-position; and $Q^5$ is selected from the group consisting of phenyl, benzyl, phenethyl and naphthyl, wherein any phenyl ring or naphthyl may bear one or more substituents selected from (1–3C)alkyl, (1–3C)alkoxy, methylenedioxy, halogeno, hydroxy, (1–4C)acyloxy and $NR^A R^B$ in which $R^A$ and $R^B$ are independently hydrogen or (1–3C)alkyl, or $R^A$ is hydrogen or (1–3C)alkyl and $R^B$ is (1–4C)acyl;

or the N-oxide of a piperidino nitrogen indicated by Δ (or of either basic piperazinyl nitrogen of $Q^1$ when $Z^a$ is nitrogen);

or a pharmaceutically acceptable salt thereof;

or a quaternary ammonium salt thereof in which the piperidino nitrogen indicated by Δ (or either basic piperazinyl nitrogen of $Q^1$ when $Z^a$ is nitrogen) is a quadricovalent ammonium nitrogen wherein the fourth radical on the nitrogen $R^1$ is (1–4C)alkyl or benzyl and the associated counterion A is a pharmaceutically acceptable anion.

A subgroup of the invention is a compound of formula III, or a pharmaceutically acceptable salt thereof, wherein $Q^1$, $Q^2$, and $Q^5$ have any of the meanings given above for a compound of formula I.

It will be appreciated that a compound of formula I (or III) contains one or more asymmetrically substituted carbon atoms such that such a compound may be isolated in optically active, racemic and/or diastereomeric forms. A compound may exhibit tautomerization. A compound may exhibit polymorphism. It is to be understood that the present invention encompasses any racemic, optically-active, diastereomeric, tautomeric, polymorphic or stereoisomeric form, or mixture thereof, which form possesses NK2 antagonist properties, it being well known in the art how to prepare optically-active forms (for example, by resolution of the racemic form or by synthesis from optically-active starting materials) and how to determine the NK2 antagonist properties by the standard tests described hereinafter. It may be preferred to use the compound of formula I (or ifi) in an optically pure form which is characterized as containing, for example, at least 95%, 98% or 99% enantiomeric excess of a particular form. For example, it may be preferred to use the compound of formula I (or III), or a particular diastereomer thereof, in a form which is characterized as containing at least 95%, 98% or 99% enantiomeric excess of the form with the (S)-configuration at the center indicated by * in the formulae.

In this specification $R^{aa}$, $R^{ab}$, $R^1$, $R^2$, et cetera stand for generic radicals and have no other significance. It is to be understood that the generic term "(1–6C)alkyl" includes both straight and branched chain alkyl radicals but references to individual alkyl radicals such as "propyl" embrace only the straight chain ("normal") radical, branched chain isomers such as "isopropyl" being referred to specifically. A similar convention applies to other generic groups, for example, alkoxy, alkanoyl, et cetera. Halo is fluoro, chloro, bromo or iodo. Aryl (except where more specifically defined) denotes a phenyl radical or an ortho-fused bicyclic carbocyclic radical having about nine to ten ring atoms in which at least one ring is aromatic. Heteroaryl (except where more specifically defined) encompasses a radical attached via a ring carbon of a monocyclic aromatic ring containing five ring atoms consisting of carbon and one to four heteroatoms selected from oxygen, sulfur and nitrogen or containing six ring atoms consisting of carbon and one or two nitrogens, as well as a radical of an ortho-fused bicyclic heterocycle of about eight to ten atoms derived therefrom, particularly a benz-derivative or one derived by fusing a propenylene, trimethylene of tetramethylene diradical thereto, as well as a stable N-oxide thereof. Aroyl is arylcarbonyl; heteroaroyl is heteroarylcarbonyl.

A pharmaceutically acceptable salt is one made with an acid which provides a physiologically acceptable anion.

Particular values are listed below for radicals or portions thereof (for example, particular values for (1–3C)alkyl provide particular values for the alkyl portion of (1–3C)alkoxy or (1–3C)alkylsulfinyl), substituents and ranges for a compound of formula I or formula III as described above for illustration only and they do not exclude other defined values or other values within defined ranges for the radicals and substituents.

A particular value for Ar is phenyl which may be unsubstituted or may bear a chloro, methyl, methoxy, hydroxy or methylsulfinyl substituent. A particular value for Het is furyl, thienyl, 2-imidazolyl, 1,3,4-oxadiazol-2-yl, pyridyl or pyrimidinyl which ring may be unsubstituted or may bear a chloro, methyl, methoxy, hydroxy, methylsulfinyl, methoxycarbonyl or ethoxycarbonyl substituent. A particular value for aryl is phenyl. A particular value for heteroaryl is furyl, pyridyl or pyrimidinyl. A particular value for halo is chloro or bromo. A particular value for (1–3C)alkyl is methyl, ethyl, propyl or isopropyl; for (1–4C)alkyl is methyl, ethyl, propyl, isopropyl, butyl, isobutyl or t-butyl; for (1–5C)alkyl is methyl, ethyl, propyl, isopropyl, butyl, isobutyl, t-butyl, pentyl or isopentyl; for (1–6C)alkyl is methyl, ethyl, propyl, isopropyl, butyl, isobutyl, t-butyl, pentyl, isopentyl, hexyl or isohexyl; and for (1–8C)alkyl is methyl, ethyl, propyl, isopropyl, isopentyl, 1-ethylpropyl, hexyl, isohexyl, 1-propylbutyl, or octyl. A particular value for (3–6C) cylcoalkyl is cyclopropyl, cyclopentyl or cyclohexyl; for (3–7C)cycloalkyl is cyclopropyl, cyclopentyl, cyclohexyl or cycloheptyl; and for (3–8C)cycloalkyl is cyclopropyl, cyclopentyl, cyclohexyl, cycloheptyl or cyclooctyl. A particular value for (3–6C)alkenyl is allyl, 2-butenyl or 3-methyl-2-butenyl. A particular value for (1–4C)alkanoyl is formyl, acetyl, propionyl, butyryl or isobutyryl; and for (1–5C)alkanoyl is formyl, acetyl, propionyl, butyryl, isobutyryl, valeryl, isovaleryl or pivaloyl.

A more particular value for Ar is phenyl which may be unsubstituted or may bear a methoxy, hydroxy or methylsulfinyl substituent. A more particular value for Het is pyridyl or pyrimidinyl which ring may be unsubstituted or may bear a methoxy, hydroxy or methylsulfinyl substituent. A more particular value for heteroaryl is pyridyl. A more particular value for halo is chloro. A more particular value for (1–3C)alkyl is methyl; for (1–4C)alkyl is methyl or ethyl; for (1–5C)alkyl is methyl, ethyl, propyl or isopropyl; for (1–6C)alkyl is methyl, ethyl, propyl, isopropyl, butyl, isobutyl or t-butyl; and for (1–8C)alkyl is methyl, ethyl, propyl, isopropyl, 1-ethylpropyl or 1-propylbutyl. A more particular value for (3–6C)cylcoalkyl is cyclopropyl or cyclopentyl; for (3–7C)cycloalkyl is cyclopropyl or cyclopentyl; and for (3–8C)cycloalkyl is cyclopropyl, cyclopentyl, cyclohexyl or cycloheptyl. A more particular value for (3–6C)alkenyl is allyl. A more particular value for (1–4C)alkanoyl is formyl or acetyl; and for (1–5C)alkanoyl is formyl, acetyl, propionyl, butyryl or isobutyryl.

A particular value for $Q^1$ is 4-benzylpiperidino, 4-(3-methoxyphenyl)piperidino, 4-(2-methylsulfinyl) phenylpiperidino, 4-(2-pyridyl)piperidino, 4-(3-pyridyl) piperidino, 4-(2-methylsulfinylpyrid-3-yl)piperidino, 4-hydroxy-4-phenylpiperidino, 4-acetamido-4-phenylpiperidino, 4-(N-phenylacetamido)piperidino, 4-(2-hydroxyethyl)piperidino, 4-(1-hydroxy-1-propylbutyl) piperidino, 4-(2-oxopyrrolidin-1-yl)piperidino, 4-(2-oxopiperidino)piperidino, 4-(2-thioxopiperidino)piperidino, 4-(2-oxoperhydropyrimidin-1-yl)piperidino, 4-ethoxycarbonyl-4-(2-oxopiperidino)piperidino, 4-methoxycarbonyl-4-(2-oxoperhydropyrimidin-1-yl) piperidino, 4-(1-oxoisoindolin-2-yl)piperidino, 4-(2-oxo-2, 3-dihydrobenzimidazol-1-yl)piperidino, 4-(2-oxo-1,2,3,4-tetrahydroquinazolin-3-yl)piperidino 4-methylaminocarbonyl-4-(2-oxopiperidino)piperidino, 4-aminocarbonyl-4-(piperidino)piperidino, 4-(3-methyl-2-oxoperhydropyrimidin-1-yl)piperidino, 4-(3-ethyl-2-oxoperhydropyrimidin-1-yl)piperidino, 4-(N,N-dimethylaminocarbonyl)-4-(2-oxopiperidino)piperidino, 4-methyl-4-(2-oxoperhydropyrimidin-1-yl)piperidino, 4-methyl-4-(2-oxoperhydropyrimnidin-1-yl)piperidino,4-(2-oxo-2,3-dihydrobenzimidazol-1-yl)piperidino, 4-(2-oxoperhydropyrimidin-1-yl)-4-(pyrrolidin-1-ylcarbonyl) piperidino, 4-(5,5-dimethyl-2-oxoperhydropyrimidin-1-yl) piperidino, or 4-methyl-4-(2-oxopiperidino)piperidino.

A particular value for $Q^2$ is tetrazol-1-yl, imidazol-1-yl, or 1,3,4-triazol-1-yl.

A particular value for $Q^3$ is hydrogen.

A particular value for $Q^4$ is 3,4-dichlorophenyl or 3,4-methylenedioxyphenyl.

A particular value for $R^1$ is methyl or benzyl and for A is, for example, chloride, bromide or methanesulfonate.

A more particular value for $Q^1$ is 4-hydroxy-4-phenylpiperidino, 4-(2-oxopyrrolidin-1-yl)piperidino, 4-acetamido-4-phenylpiperidino, 4-acetamido-4-(2-oxopiperidino)piperidino, 4-ethoxycarbonyl-4-(2-oxopiperidino)piperidino, 4-methoxycarbonyl-4-(2-oxopiperidino)piperidino, 4-methylaminocarbonyl-4-(2-oxopiperidino)piperidino, 4-(dimethylamino)carbonyl-4-(2-oxopiperidino)piperidino, 4-aminocarbonyl-4-(piperidino) piperidino, 4-(3-methyl-2-oxoperhydropyrimidin-1-yl) piperidino, 4-(3-ethyl-2-oxoperhydropyrimidin-1-yl)

piperidino, 4-methyl-4-(2-oxopiperidino)piperidino, 4-methyl-4-(2-oxoperhydropyrimidin-1-yl)piperidino, 4-(2-oxo-2,3-dihydrobenzimidazol-1-yl)piperidino, 4-(2-oxoperhydropyrimidin-1-yl)-4-(pyrrolidin-1-ylcarbonyl)piperidino, or 4-(5,5-dimethyl-2-oxoperhydropyrimidin-1-yl)piperidino.

A more particular value for $Q^2$ is imidazol-1-yl.

A particular group of compounds of formula I (or formula III) is one in which $Q^1$ is selected from a radical of formula Ia, Ib, Ic, Id, Ie, If, Ig, Ih, Ij, Ik or Im; or a pharmaceutically acceptable salt thereof.

A particular group of compounds of formula I (or formula III) is one in which $Q^1$ is selected from a combination of the radicals of formula Ia, Ib, Ic, Id, Ie, If, Ig, Ih, Ij, Ik, and Im; or a pharmaceutically acceptable salt thereof.

A particular group of compounds of formula I is one in which $J^e$, $J^f$, $J^g$, $J^i$, $J^{ja}$, $J^k$ and $J^{ka}$ are oxygen and $J^h$ is oxo; $Q^2$ represents one of the more particular values listed above for $Q^2$; $Q^3$ is hydrogen; $Q^4$ is phenyl which may bear one or two substituents selected from halo, trifluoromethyl and methylenedioxy; and $Q^5$ is phenyl; or a pharmaceutically acceptable salt thereof.

A more particular group of compounds of formula I is one in which $Q^1$ is a radical of of formula If, Ih or, Ij and wherein J is oxygen and in which the radicals and substituents may have any of the values, particular values or more particular values defined above; or a pharmaceutically acceptable salt thereof.

For compounds of the invention that include groups which may be substituted by "one or more" substituents as defined above, the term "one or more" may preferably be 1, 2, 3, or 4.

Specific compounds of formula I (and of formula III) are described in the accompanying Examples.

Pharmaceutically acceptable salts of a compound of formula I (or of formula III) include those made with a strong inorganic or organic acid which affords a physiologically acceptable anion, such as, for example, hydrochloric, sulfuric, phosphoric, methanesulfonic, or para-toluenesulfonic acid.

A compound of formula I (or of formula III) may be made by processes which include processes known in the chemical art for the production of structurally analogous heterocyclic compounds. Such processes and intermediates for the manufacture of a compound of formula I (or of formula III) as defined above are provided as further features of the invention and are illustrated by the following procedures in which the meanings of generic radicals are as defined above unless otherwise indicated:

(a) For a compound of formula I in which Z denotes a nitrogen (or for a compound of formula III), alkylating a piperidine of formula IIIa (wherein $Q^{1a}$ is a radical of formula $Q^1$ defined above for a compound of formula I in which Z denotes a nitrogen) with an aldehyde of formula IV, by reductive alkylation. The alkylation is preferably carried out by a conventional reductive alkylation, for example as described in Example 1, by the in situ, acid-catalyzed formation of an imminum salt, followed by reduction with sodium cyanoborohydride in alcoholic solvent.

(b) Alkylating a piperidine of formula IIIa with an alkylating agent of formula V in which Y is a leaving group. Typical values for Y include for example, iodide, bromide, methanesulfonate, p-toluenesulfonate, trifluoromethane-sulfonate, and the like. The reaction may be carried out under standard conditions, for example in a suitable solvent at a temperature in the range of −20° to 100° C., preferably in the range of 0° to 50° C.

(c) For an N-oxide of the piperidino nitrogen indicated by Δ in a compound of formula I (or of formula III), oxidizing the piperidino nitrogen indicated by Δ in a corresponding compound of formula I using a conventional procedure, such as, for example, using hydrogen peroxide in methanol, peracetic acid, 3-chloroperoxybenzoic acid in an inert solvent (such as dichloromethane) or dioxirane in acetone.

(d) For a quaternary ammonium salt of the piperidino nitrogen indicated by Δ in a compound of formula I (or of formula III), alkylating the piperidino nitrogen indicated by Δ in a compound of formula I (or of formula III) with an alkylating agent of formula $R^1Y$ or alkylating a piperidine of formula IIIb with an alkylating agent of formula V, wherein Y is a leaving group, followed, if required, by exchanging the counterion Y for a different counterion A by a conventional method. Typical values for Y include those listed above. Exchange of counterions may conveniently be carried out using a basic ion exchange resin in the "A" form.

(e) For a compound of formula I in which $Q^1$ is of formula Id, reducing the double bond of a corresponding starting material of formula VI using a conventional method.

(f) For a compound of formula I in which $Q^1$ is of formula Id, substituting the nitrogen of a compound of formula VIa with a radical of formula $R^{da}$—$(X^d)_p$—$Z^d$— using a conventional method.

(g) For a compound of formula I (or of formula III) which bears a sulfinyl group, oxidizing the sulfur of a corresponding compound of formula I (or of formula III) which bears a sulfide group using a conventional method.

(h) For a compound of formula I (or of formula III) which bears a sulfonyl group, oxidizing a sulfide or sulfinyl group of a corresponding compound of formula I (or of formula III) using a conventional method.

(i) For a compound of formula I (or of formula III) which bears an aromatic hydroxy group, cleaving the ether of a corresponding compound of formula I (or of formula III) which bears an aromatic alkoxy group using a conventional method.

It may be desired to optionally use a protecting group during all or portions of the above described processes; the protecting group then may be removed when the final compound is to be formed.

Whereafter, for any of the above procedures, when a pharmaceutically acceptable salt of a compound of formula I is required, it may be obtained by reacting the compound of formula I with an acid affording a physiologically acceptable counterion or by any other conventional procedure.

It will also be appreciated that certain of the various optional substituents in the compounds of the invention may be introduced by standard aromatic substitution reactions or generated by conventional functional group modifications either prior to or immediately following the processes above, and as such are included in the process aspect of the invention. Such reactions and modifications include, for example, introduction of nitro or halogeno and reduction of nitro. The reagents and reaction conditions for such procedures are well known in the chemical art.

If not commercially available, the necessary starting materials for the above procedures may be made by procedures which are selected from standard techniques of heterocyclic chemistry, techniques which are analogous to the synthesis of known, structurally similar compounds (particularly those described in the above noted EPA publications and their counterparts), and techniques which are analogous to the above described procedures or the procedures described in the Examples below. The starting materials and the procedures for their preparation are additional aspects of the invention.

As will be clear to one skilled in the art, a variety of sequences is available for preparation of the starting materials, and the sequences leading to the starting materials and products of the invention may be altered if appropriate considerations regarding the synthetic methods and radicals present are followed.

The utility of a compound of the invention or a pharmaceutically acceptable salt thereof (hereinafter, collectively referred to as a "Compound") may be demonstrated by standard tests and clinical studies, including those disclosed in the EPA publications noted above, such as EPA 428434 or EPA 474561 (or U.S. Pat. No. 5,236,921), and those described below.

Neurokinin A (NKA) Receptor-binding Assay (Test A)

The ability of a Compound of the invention to antagonize the binding of NKA at the NK2 receptor may be demonstrated using an assay using the human NK2 receptor expressed in Mouse Erythroleukemia (MEL) cells, as described in: Aharony, D., Little, J., Thomas, C., Powell, S., Berry, D. and Graham, A. Isolation and Pharmacological Characterization of a Hampster Neurokinin A Receptor cDNA, *Molecular Pharmacology*, 1994, 45, 9–19. In an initial use of this assay, the $IC_{50}$ measured for the standard compound L-659,877 was found to be 30 nM versus $^3$H-NKA binding to MEL.

The selectivity of a Compound for binding at the NK2 receptor may be shown by determining its binding at other receptors using standard assays, for example, one using a tritiated derivative of SP in a tissue preparation selective for NK1 receptors or one using a tritiated derivative of NKB in a tissue preparation selective for NK3 receptors.

Guinea Pig Assay (Test B)

The ability of a Compound of the invention to antagonize the action of an agonist, either NKA or [b-ala$^8$]-NKA(4–10), in a pulmonary tissue may be demonstrated using a functional assay in guinea pig trachea, which is carried out in a manner similar to that described in International Patent Application Publication Number WO 94/10146 beginning at pages 19–20.

Clinical studies to demonstrate the efficacy of a Compound of the invention may be carried out using standard methods. For example, the ability of a Compound to prevent or treat the symptoms of asthma or asthma-like conditions may be demonstrated using a challenge of inhaled cold air or allergen and evaluation by standard pulmonary measurements such as, for example, $FEV_1$ (forced expiratory volume in one second) and FVC (forced vital capacity), analyzed by standard methods of statistical analysis.

It will be appreciated that the implications of a Compound's activity in Test A or Test B is not limited to asthma, but rather, that the test provides evidence of general antagonism of NKA. In general, the Compounds of the invention which were tested demonstrated statistically significant activity in Test A with a $K_i$ of 1 mM or much less. For example, the compound described in Example 2 was found to have a $K_i$ of 23 nM. In Test B, a $pK_B$ of 5 or greater was typically measured for a Compound of the invention. For example, a $pK_B$ of 8.7 was measured for the compound described in Example 3.

As discussed above, a compound of formula I or a pharmaceutically acceptable salt thereof possesses NKA antagonist properties. Accordingly, it antagonizes at least one of the actions of NKA which are known to include bronchoconstriction, increased microvascular permeability, vasodilation and activation of mast cells. Accordingly, one feature of the invention is the use of a compound of formula I or a pharmaceutically acceptable salt thereof in the treatment of a disease in a human or other mammal in need thereof in which NKA is implicated and antagonism of its action is desired, such as for example the treatment of asthma or a related disorder. In addition, another feature of the invention is provided by the use of a compound of formula I or a salt thereof as a pharmacological standard for the development and standardization of new disease models or assays for use in developing new therapeutic agents for treating the diseases in which NKA is implicated or for assays for their diagnosis. When used in the treatment of such a disease, a compound of the invention is generally administered as an appropriate pharmaceutical composition which comprises a compound of formula I or a pharmaceutically acceptable salt thereof as defined hereinbefore and a pharmaceutically acceptable diluent or carrier, the composition being adapted for the particular route of administration chosen. Such a composition is provided as a further feature of the invention. It may be obtained employing conventional procedures and excipients and binders, and it may be one of a variety of dosage forms. Such forms include, for example, tablets, capsules, solutions or suspensions for oral administration; suppositories for rectal administration; sterile solutions or suspensions for administration by intravenous or intramuscular infusion or injection; aerosols or nebulizer solutions or suspensions for administration by inhalation; or powders together with pharmaceutically acceptable solid diluents such as lactose for administration by insufflation.

For oral administration a tablet or capsule containing up to 250 mg (and typically 5 to 100 mg) of a compound of formula I may conveniently be used. For administration by inhalation, a compound of formula I will be administered to humans in a daily dose range of, for example, 5 to 100 mg, in a single dose or divided into two to four daily doses. Similarly, for intravenous or intramuscular injection or infusion a sterile solution or suspension containing up to 10% w/w (and typically 0.05 to 5% w/w) of a compound of formula I may conveniently be used.

The dose of a compound of formula I to be administered will necessarily be varied according to principles well known in the art taking account of the route of administration and the severity of the condition and the size and age of the patient under treatment. However, in general, the compound of formula I will be administered to a warm-blooded animal (such as man) so that a dose in the range of, for example, 0.01 to 25 mg/kg (and usually 0.1 to 5 mg/kg) is received. It will be understood that generally equivalent amounts of a pharmaceutically acceptable salt of a compound of formula I may be used.

The invention will now be illustrated by the following non-limiting examples in which, unless stated otherwise:

(i) temperatures are given in degrees Celsius (°C.); operations were carried out at room or ambient temperature, that is, at a temperature in the range of 18°–25° C.;

(ii) organic solutions were dried over anhydrous magnesium sulfate; evaporation of solvent was carried out using a rotary evaporator under reduced pressure (600–4000 pascals; 4.5–30 mm Hg) with a bath temperature of up to 60° C.;

(iii) chromatography means flash chromatography on silica gel; reversed phase chromatography means chromatography over octadecylsilane (ODS) coated support having a particle diameter of 32–74 m, known as "PREP-40-ODS" (Art 731740-100 from Bodman Chemicals, Aston, Pa., USA); thin layer chromatography (TLC) was carried out on silica gel plates; radial chromatography refers to chromatography on circular thin layer silica gel plates (Analtech) on a Harrison Research Model 8924 Chromatotron.

(iv) in general, the course of reactions was followed by TLC and reaction times are given for illustration only;

(v) melting points are uncorrected and (dec) indicates decomposition; the melting points given are those obtained for the materials prepared as described; polymorphism may result in isolation of materials with different melting points in some preparations;

(vi) final products had satisfactory proton nuclear magnetic resonance (NMR) spectra;

(vii) yields are given for illustration only and are not necessarily those which may be obtained by diligent process development; preparations were repeated if more material was required;

(viii) when given, NMR data is in the form of delta values for major diagnostic protons, given in parts per million (ppm) relative to tetramethylsilane (TMS) as an internal standard, determined at 300 MHz using perdeuterio dimethyl sulfoxide (DMSO-$d_6$) as solvent; conventional abbreviations for signal shape are used; for AB spectra the directly observed shifts are reported; coupling constants (J) are given in Hz; Ar designates an aromatic proton when such an assignment is made;

(ix) chemical symbols have their usual meanings; SI units and symbols are used;

(x) reduced pressures are given as absolute pressures in pascals (Pa); elevated pressures are given as gauge pressures in bars;

(xi) solvent ratios are given in volume:volume (v/v) terms; and (xii) mass spectra (MS) were run with an electron energy of 70 electron volts in the electron i exposure probe; where indicated ionization was effected by chemical ionization (CI) or fast atom bombardment (FAB); values for m/z are given; generally, only ions which indicate the parent mass are reported.

EXAMPLE 1

1-[3-(3,4-Dichlorophenyl)-4-(5-phenyltetrazol-1-yl)butyl]-4-hydroxy-4-phenylpiperidine.

3-(3,4-Dichlorophenyl)-4-(5-phenyltetrazol-1-yl) butyraldehyde (0.200 g) in methanol (1 mL) and dichloromethane (1 mL) was added to a solution of 4-hydroxy-4-phenylpiperidine (0.147 g) and acetic acid (0.047 mL) in methanol (1 mL). After 2 minutes, sodium cyanoborohydride (52 mg) in methanol (1 mL) was added in a single portion. After being stirred overnight, the reaction mixture was diluted with aqueous sodium bicarbonate, stirred for 30 minutes, and extracted with dichloromethane. The organic extracts were dried and evaporated. The crude product was suspended in methanol/ether and filtered to give the title compound as a white solid (0.13 g); NMR: 7.57 (m,5), 7.44 (m,2), 7.36–7.18 (m,5), 6.87 (dd,1, J=1.6, 8.2), 4.98 (dd,1, J=5.2, 14.3), 4.81 (dd,1, J=10.1, 14.2), 4.71 (s,1), 3.20 (m,1), 2.54 (m,1), 2.34–2.16 (m,3), 2.09 (m,2), 1.91 (m,1), 1.75 (m,3), 1.50 (m,2); MS; m/z=522(M+1). Analysis for $C_{28}H_{29}Cl_2N_5O$: Calculated: C, 64.37; H, 5.59; N, 13.40; Found: C, 64.10; H, 5.56; N, 13.28.

The intermediate aldehyde was prepared as follows:

a. 1-Bromo-2-(tetrahydropyran-2-yloxy)ethane. To a mechanically stirred solution of dihydropyran (1000 mL) and a strong acid ion exchange resin (10.0 g) in hexane (2 L) was added 2-bromoethanol (985 g) dropwise over a period of 1.5 hours in a cold water bath to maintain an internal temperature of 35°–40° C. After being stirred overnight at room temperature, the reaction mixture was chromatographed, eluting with hexane (6 L). The eluate was evaporated to give an amber liquid which was distilled through a 2 inch vigreux column collecting the material boiling between 75°–95° C. (3,300–4,700 Pa). This material was redistilled to give the ether as an oil (1195.5 g); bp 80°–90° C. (2666 Pa); NMR: 4.68 (m,1), 4.01 (m,1), 3.89 (m,1), 3.77 (m,1), 3.52 (m,3), 1.75–1.50 (m,6).

b. α-[2-(Tetrahydropyran-2-yloxy)ethyl]-3,4-dichlorophenyl-acetonitrile. To a solution of sodium hydride (218.0 g of a 55% oil suspension) in tetrahydrofuran (4 L) at 10° C. in an ice/water bath was added 3,4-dichlorophenylacetonitrile (893.0 g) in tetrahydrofuran (2 L) over a period of 45 minutes, and the resulting solution was allowed to stir for 2 hours at room temperature. The mixture was cooled in an ice/water bath and 1-bromo-2-(tetra-hydropyran-2-yloxy)ethane (1076.0 g) was dropped in as a neat oil over a period of 25 minutes. The mixture was stirred overnight at room temperature and divided into four 2-liter portions. Each portion was diluted with saturated ammonium chloride (3 L) and extracted with ether (500 mL). The combined organic layers were washed (aqueous ammonium chloride), dried, and evaporated. The resulting material was chromatographed, with hexane:dichloromethane (gradient 100:0, 0:100) as eluent, to give the nitrile as an oil (932 g); NMR: 7.47 (m,4), 7.20 (m,2), 4.57 (m,2), 4.08 (m,2), 3.85 (m,4), 3.54 (m,3), 3.37 (m,1), 2.15 (m,4), 1.77 (m,4), 1.56 (m,8).

c. 2-(3,4-Dichlorophenyl)-4-(tetrahydropyran-2-yloxy) butyl-amine. To a solution of the above nitrile (128.3 g) in 95% ethanol (1.1 L) and concentrated ammonium hydroxide (550 mL) was added Raney Nickel (25.0 g). The mixture was hydrogenated under a hydrogen atmosphere at 3.6 bars for 1.5 days. The mixture was filtered through diatomaceous earth to remove the catalyst, and the resulting filtrate was evaporated. The resulting material was chromatographed, with dichloromethane:methanol (gradient 100:0, 95:5) as eluent, to give the amine as an oil (91 g); NMR: 7.40 (s,1), 7.38 (s,1), 7.32 (d,1, J=2.1), 7.28 (d,1, J=2.0), 7.07 (dd,1, J=2.1, 4.9), 7.04 (dd,1, J=2.1, 4.9), 4.50 (m,1), 4.43 (m,1), 3.70 (m,4), 3.45 (m,2), 3.27 (m,1), 3.17 (m,1), 2.97–2.75 (m,6), 2.00 (m,2), 1.82–1.66 (m,6), 1.53 (m, 1.18 (broad s,4); MS: m/z=318(M+1).

d. N-[2-(3,4-Dichlorophenyl)-4-(tetrahydropyran-2-yloxy)butyl]-benzamide. To a solution of the above amine (2.5 g) in dichloromethane (35 mL) was added triethylamine (1.1 mL) and benzoic anhydride (1.85 g), and the resulting solution was allowed to stir for 45 minutes. The mixture was washed (0.2N hydrochloric acid, 1N sodium hydroxide, water), dried, and evaporated to give the amide as an oil (3.3 g); NMR: 7.63 (m,4), 7.46 (m,2), 7.37 (m,8), 7.09 (m,2), 6.22 (m,2), 4.50 (m,1), 4.43 (m,1), 3.8 (m,5), 3.63 (m,1), 3.5 (m,4), 3.36 (m,1), 3.23 (m,1), 3.11 (m,2), 2.06 (m,2), 1.90–1.77 (m,4), 1.68 (m,2), 1.51 (m,8); MS: m/z=338 [(M+1)-tetrahydropyranyl].

e. N-[2-(3,4-Dichlorophenyl)-4-hydroxybutyl] benzamide. A solution of the above ether (4.0 g) in tetrahydrofuran (20 mL) and 3N hydrochloric acid (20 mL) was stirred for 2 hours. The reaction mixture was diluted with water, neutralized with 1N sodium hydroxide, and extracted with dichloromethane. The organic extracts were dried, evaporated, and chromatographed, with dichloromethane:methanol (95:5) as eluent, to give the hydroxy benzamide compound as a viscous oil (2.9 g); NMR: 7.63 (m,2), 7.47 (m,1), 7.37 (m,3), 7.32 (d,1, J=2.1), 7.06 (dd,1, J=2.1, 8.3), 6.46 (m,1), 3.82 (m,1), 3.69 (m,1), 3.57–3.39 (m,2), 3.12 (m,1), 2.60 (m,1), 1.97 (m,1), 1.82 (m,1); MS: m/z=338(M+1).

f. Acetic acid 4-benzoylamino-3-(3,4-dichlorophenyl) butyl ester. The above alcohol (2.9 g) in dichloromethane (3 mL) was added to a solution of pyridine (0.90 mL) and acetyl chloride (0.67 mL) in dichloromethane (37 mL). After being stirred for 1.5 hours, the reaction mixture was washed (water, saturated aqueous copper(II) sulfate, and water), and the separated organic phase was dried and evaporated to give the ester as a viscous oil (3.0 g); NMR: 7.63 (m,2), 7.48 (m,1), 7.39 (m,3), 7.32 (d,1, J=2.1), 7.06 (dd,1, J=2.1, 8.2), 6.21 (m,1), 4.03 (m,1), 3.87 (m,2), 3.41 (m,1), 3.07 (m,1), 2.09 (m,1), 1.98 (s,3), 1.92 (m,1); MS: m/z=380(M+1)

g. 3-(3,4-Dichlorophenyl)-4-(5-phenyltetrazol-1-yl) butan-1-ol. A solution of the above amide (1.0 g) and phosphorus pentachloride (0.548 g) in toluene (20 mL) was heated at 80° C. for 2 hours and then at reflux briefly. The mixture was evaporated to a viscous, yellow oil and dissolved in N,N-dimethylformamide (12 mL) containing sodium azide (0.845 g). After being stirred for 2 days, the reaction mixture was diluted with water (700 mL) and extracted with dichloromethane. The organic extracts were dried, evaporated, and dissolved in methanol (4 mL) and 50% w/w sodium hydroxide (0.16 mL). After being stirred for 45 minutes, the mixture was diluted with 1N hydrochloric acid/water and extracted with dichloromethane. The organic extracts were dried and evaporated to give the alcohol (0.845 g) as a solid which was contaminated with an undetermined amount of the benzamide from 1e; the crude product was used in the next step without purification; MS: m/z=363(M+1).

h. 3-(3,4-Dichlorophenyl)-4-(5-phenyltetrazol-1-yl) butyraldehyde. To a solution of oxalyl chloride (0.28 mL) in dichloromethane (8 mL) at −78° C. was added methyl sulfoxide (0.46 mL) in dichloromethane (4 mL). After 5 minutes, 3-(3,4-dichlorophenyl)-4-(5-phenyltetrazol-1-yl)butan-1-ol (0.840 g) contaminated with an undetermined amount of N-[2-(3,4-dichlorophenyl)-4-hydroxybutyl]benzamide) in dichloromethane (4 mL) was dropped in, and the mixture was stirred for 25 minutes. Triethylamine (1.81 mL) was then added and the solution was allowed to gradually warm to ambient temperature. The reaction mixture was washed (1N hydrochloric acid, aqueous sodium bicarbonate, water), and the separated organic phase was dried and evaporated. The crude product was chromatographed, with ether:hexane (5:1) as eluent, to give the aldehyde (0.212 g) as a white solid; NMR: 9.70 (m,1), 7.49 (m,3), 7.29 (m,2), 7.18 (d,1, J=8.2), 6.89 (d,1, J=1.6), 6.63 (dd,1, J=8.1, 1.8), 4.76 (dd,1, J=5.8, 13.9), 4.58 (dd,1, J=7.8, 13.9), 3.81 (m,1), 3.04 (dd,1, J=7.3, 18.5), 2.88 (dd,1, J=6.9, 18.5); MS: m/z=361 (M+1).

EXAMPLE 2

1-[3-(3,4-Dichlorophenyl)-4-(2-phenylimidazol-1-yl)butyl]-4-hydroxy-4-phenylpiperidine dihydrochloride.

3-(3,4-Dichlorophenyl)-4-(2-phenylimidazol-1-yl) butyraldehyde (1.0 g) in methanol (7 mL) was added to a solution of 4-hydroxy-4-phenylpiperidine (0.741 g) and acetic acid (0.24 mL) in methanol (7 mL). After 5 minutes, sodium cyanoborohydride (0.263 g) in methanol (7 mL) was added in a single portion. After being stirred for 2 hours, the reaction mixture was diluted with aqueous sodium bicarbonate, stirred for 30 minutes, and extracted with dichloromethane. The organic extracts were dried, evaporated, and chromatographed, with dichloromethane:methanol (gradient 98:2, 90:10) as eluent. The purified material was dissolved in dichloromethane, precipitated out as the hydrochloride salt with ethereal hydrogen chloride, evaporated, and placed under high vacuum overnight to give the title compound as a white solid (0.760 g); NMR: 7.92 (m,1), 7.69 (m,2), 7.59 (m,2), 7.50 (m,2), 7.36 (m,2), 7.28 (m,4), 7.10 (d,1, J=2.1), 6.85 (dd,1, J=2.1, 8.3), 4.70 (dd,1, J=4.5, 14.0), 4.57 (dd,1, J=10.5, 13.9), 3.47 (m,3), 3.27 (m,2), 3.14 (m,1), 2.84 (m,1), 2.47–2.20 (m,4), 1.93 (m,2); MS: m/z=520(M+1) Analysis for $C_{30}H_{31}Cl_2N_3O.02.80$ HCl.0.15 $Et_2O$: Calculated: C, 58.00; H, 5.61; N, 6.63; Found: C, 57.99; H, 5.80; N, 6.77.

The intermediate aldehyde was prepared as follows:

a. Acetic acid-3-(3,4-Dichlorophenyl)-4-[(2,2-dimethoxyethylimino)-phenylmethyl]amino butyl ester and acetic acid 3-(3,4-dichlorophenyl)-4-[(2,2-dimethoxy]ethylamino)phenylmethyleneamino]butyl ester. A solution of acetic acid 4-benzoylamino-3-(3,4-dichlorophenyl)butyl ester (1.5 g, from Example 1f) in thionyl chloride (4.0 mL) was vigorously refluxed for 1 hour. The reaction mixture was diluted with toluene and evaporated. To the resulting residue in N,N-dimethylformamide (5 mL) cooled to 0° C. was added 2,2-dimethoxyethylamine (0.47 mL) in N,N-dimethylformamide (5 mL). After being stirred for 20 minutes, the mixture was diluted with aqueous sodium bicarbonate and extracted with dichloromethane. Due to incomplete extraction, the combined dichloromethane extracts were poured back into the separatory funnel with the aqueous phase and acidified with dilute aqueous hydrochloric acid. The dichloromethane layer was washed with water, dried, and evaporated. Chromatography, with dichloromethane:methanol (gradient 95:5, 70:30) as eluent, gave the aldehyde as a viscous oil (1.4 g); MS: m/z=467(M+1).

b. Acetic acid 3-(3,4-Dichlorophenyl)-4-(2-phenylimidazo-1-yl)butyl ester. A solution of the above amidine (1.2 g) and p-toluenesulfonic acid monohydrate (0.540 mg) in toluene (25 mL) was refluxed for 2 hours with azeotropic removal of water using a Dean-Stark trap. The mixture was evaporated, diluted with dichloromethane, and washed with saturated aqueous sodium bicarbonate. The separated organic phase was dried and evaporated to give a mixture of the imidazolyl ester (1.0 g) and 3-(3,4-dichlorophenyl)-4-(2-phenylimidazo-1-yl)butan-1-ol as a light-brown, viscous oil; the crude product was used in the next step without purification; MS: m/z=403(M+1), 361(M+1).

c. 3-(3,4-Dichlorophenyl)-4-(2-phenylimidazo-1-yl) butan-1-ol. A solution of the ester (1.4 g) in tetrahydrofuran (40 mL), water (16 mL), 1N sodium hydroxide (7 mL), and methanol (2 mL) was stirred for 2 hours. After the volatile organics were evaporated, the resulting aqueous mixture was diluted with water and extracted with dichloromethane. The combined organic extracts were dried and evaporated to give the imidazolyl alcohol (1.0 g); the crude product was used in the next step without purification; MS: m/z=361(M+1).

d. 3-(3,4-Dichlorophenyl)-4-(2-phenylimidazo-1-yl) butyraldehyde. The above alcohol (1.0 g) in dichloromethane (5 mL) was cannulated into a solution of Dess-Martin periodinane (1.7 g) and tert-butanol (0.52 mL) in dichloromethane (25 mL). After being stirred for 5 minutes, the reaction mixture was diluted with ether (25 mL) and a solution of sodium bicarbonate (2.4 g) and sodium thiosulfate pentahydrate (7.9 g) in water (100 mL). The biphasic system was vigorously stirred until both layers became clear (approximately 30 minutes). The separated organic layer was washed (saturated aqueous sodium bicarbonate), dried, and evaporated. Chromatography, with dichloromethane:methanol (gradient 95:5, 80:20) as eluent, gave the aldehyde as a foamy, white solid (1.0 g); NMR (CDCL$_3$/CF$_3$COOH): 9.67 (m,1), 7.67 (m,1), 7.52 (m,2), 7.45 (m,1), 7.35 (m,1), 7.22 (m,1), 7.13 (m,2), 6.82 (d,1, J=2.1), 6.62 (dd,1, J=2.2, 8.3), 4.52 (dd,1, J=4.3, 13.8), 4.34 (dd,1, J=10.5, 13.8), 3.54 (m,1), 2.96 (m,2); MS: m/z=359(M+1).

EXAMPLE 3

1-[1-[3-(3,4-Dichlorophenyl)-4-(2-phenyl-1,3,4-triazol-1-yl)butyl]piperidin-4-yl] tetrahydropyrimidin-2-one hydrochloride.

3-(3,4-Dichlorophenyl)-4-(2-phenyl-1,3,4-triazol-1-yl) butyroldehyde (0.80 g) in methanol (4 mL) was added to a solution of 1-(piperidin-4-yl)tetrahydropyrimidin-2-one (0.408 g) and acetic acid (0.13 mL) in methanol (4 mL). After 40 minutes, sodium cyanoborohydride (0.140 g) in methanol (4 mL) was added in a single portion. After being stirred overnight, the reaction mixture was diluted with aqueous sodium bicarbonate, stirred for 30 minutes, and extracted with dichloromethane. The organic extracts were dried, evaporated, and chromatographed, with dichloromethane:methanol (gradient 95:5, 70:30) as eluent. The purified material was dissolved in dichloromethane, precipitated out as the hydrochloride salt with ethereal hydrogen chloride, evaporated, and placed under high vacuum overnight to give the title compound as a white solid (1.0 g); NMR (CD$_3$OD): 9.55 (s,1), 7.74 (m,1), 7.62 (m,2), 7.42 (m,2), 7.29 (d,1, J=8.3), 7.16 (d,1, J=2.1), 6.89 (dd,1, J=2.1, 8.3), 4.83 (dd,1, J=4.7, 14.3), 4.64 (dd,1, J=10.2, 14.2), 4.36 (m,1), 3.60 (m,2), 3.26 (m,5), 3.03 (m,3), 2.75 (m,1), 2.22 (m,4), 1.91 (m,4); MS: m/z=527(M+1). Analysis for C$_{27}$H$_{32}$Cl$_2$N$_6$O.4.20HCl.0.20 Et$_2$O: Calculated: C, 48.01; H, 5.53; N, 12.08; Found: C, 48.09; H, 5.64; N, 12.06.

The intermediate aldehyde was prepared as follows:

a. Acetic acid 3-(3,4-Dichlorophenyl)-4-(2-phenyl-1,3,4-triazol-1-yl)butyl ester. A solution of acetic acid 4-benzoylamino-3-(3,4-dichlorophenyl)butyl ester (3.0 g, from Example 1f) in thionyl chloride (16 mL) was vigorously refluxed for 1 hour. The reaction mixture was diluted with toluene and evaporated. To the resulting residue in N,N-dimethylfornamide (8 mL) cooled to 0° C. was added formic hydrazide (0.526 g) as a solid. After being stirred for 20 minutes, the mixture was diluted with water and extracted with dichloromethane. The aqueous phase was acidified (pH=3) with hydrochloric acid and extracted with dichloromethane. Due to incomplete extraction, the aqueous phase was basified (pH=10) with sodium hydroxide and extracted with ethyl acetate. The aqueous phase was again acidified (pH=3) and extracted with dichloromethane. The combined organic extracts were dried, evaporated, and chromatographed, with dichloromethane:methanol (gradient 98:2, 90:10) as eluent, to give the triazolyl ester as a viscous, orange-red oil (2.4 g); NMR (CD$_3$OD): 8.50 (s,1), 7.53 (m,3), 7.37 (m,2), 7.25 (d,1, J=8.3), 7.01 (d,1, J=2.1), 6.76 (dd,1, J=2.1, 8.3), 4.55 (dd,1, J=5.1, 14.3), 4.34 (dd,1, J=10.4, 14.2), 3.96 (m,1), 3.76 (m,1), 2.98 (m,1), 1.96 (m,2), 1.89 (s,3); MS: m/z=404(M+1).

b. 3-(3,4-Dichlorophenyl)-4-(2-phenyl-1,3,4-triazol-1-yl) butan-1-ol. Using the procedure similar to Example 2c, acetic acid 3-(3,4-Dichlorophenyl)-4-(2-phenyl-1,3,4-triazol-1-yl)butyl ester, was transformed into the desired alcohol which was obtained as a white solid; NMR (CDCl$_3$): 8.06 (s,1), 7.48 (m,3), 7.36 (m,2), 7.23 (d,1, J=8.2), 6.94 (d,1, J=2.1), 6.67 (dd,1, J=2.1, 8.2), 4.39 (dd,1, J=5.6, 14.1), 4.17 (dd,1, J=9.5, 14.1), 3.59 (m,1), 3.38 (m,1), 3.13 (m,1), 2.05 (m,1), 1.88 (m,1), 1.75 (m,1); the crude product was used in the next step without purification; MS: m/z=362(M+1).

c. 3-(3,4-Dichlorophenyl)-4-(2-phenyl-1,3,4-triazol-1-yl) butyraldehyde. Dess-Martin periodinane (4.2 g) was added in a single portion to a solution of the above alcohol (1.8 g) in acetonitrile (75 mL), resulting in the immediate formation of a white precipitate. After being stirred for 10 minutes, the reaction mixture was diluted with an aqueous solution (100 mL) of sodium bicarbonate (2.4 g) and sodium thiosulfate pentahydrate (7.9 g). The biphasic system was vigorously stirred until both layers became clear, diluted with water, and extracted with dichloromethane. The organic extracts were dried, evaporated, and chromatographed, with dichloromethane:methanol (gradient 95:5, 80:20) as eluent, to give the aldehyde as a foamy, white solid (1.7 g); NMR (CDCl$_3$/CF$_3$COOH): 9.66 (m, 1), 9.21 (s,1), 7.75 (m, 1), 7.61 (m,2), 7.37 (m,2), 7.27 (m,1), 6.90 (d,1, J=2.1), 6.70 (dd,1, J=2.2, 8.3), 4.75 (dd,1, J=4.9, 14.1), 4.49 (dd,1, J=10.1, 14.1), 3.54 (m, 1), 3.01 (m, 2); MS: m/z=360(M+1).

The intermediate piperidine was prepared as follows:

d. 8-Benzyloxycarbonyl-1,4-dioxa-8-azaspiro[4.5] decane. Benzyl chloroformate (57.0 g) was added dropwise to a solution of 1,4-dioxa-8-azaspiro[4.5]decane (50.2 g) and pyridine (54.0 mL) in dichloromethane (300 mL) at −5° C. Upon complete addition, the mixture was allowed to warm to ambient temperature and was stirred overnight. The mixture was washed successively with 1N hydrochloric acid and aqueous sodium bicarbonate. The separated organic phase was dried and evaporated to give the ketal as an oil (92.9 g); NMR (CDCl$_3$): 7.35 (m,5), 5.13 (s,2), 3.96 (s,4), 3.59 (m,4), 1.67 (m,4); the crude product was used in the next step without purification; MS: m/z=278(M+1)

e. 4-Oxopiperidine-1-carboxylic acid benzyl ester. A solution of the above ketal (92.9 g) in trifluoroacetic acid (100 mL) and water (20 mL) was heated at 50° C. for 1.5 hours, followed by a 2 minute reflux. The mixture was evaporated, neutralized with saturated aqueous sodium bicarbonate, diluted with water, and extracted with dichloromethane. The organic extracts were dried, evaporated, and distilled (156°–164° C., 11.33–12.00 Pa) to give the title compound as a colorless liquid (59 g); NMR (CDCl$_3$): 7.37 (m,5), 5.18 (s,2), 3.80 (m,4), 2.46 (m,4); MS: m/z=234(M+1).

f. 4-(3-Aminopropylamino)piperidine-1-carboxylic acid benzyl ester. The above ketone (32.0 g) in methanol (250 mL) was added to a solution of 1,3-diaminopropane (17.2 mL) and acetic acid (23.6 mL) in methanol (250 mL). After 30 minutes, sodium cyanoborohydride (25.9 g) in methanol (250 mL) was added in a single portion. After being stirred overnight, the mixture was concentrated in vacuo and the resulting residue was dissolved in 1N hydrochloric acid (100 mL). Concentrated hydrochloric acid was added dropwise and stirring was continued until the evolution of gas ceased. The acidic aqueous mixture was extracted with dichloromethane (discarded), basified to pH 10 with 10N sodium hydroxide, and extracted with dichloromethane. The latter dichloromethane extracts were dried and evaporated to give the benzyl ester as a viscous, light yellow oil (25.4 g); NMR (CD$_3$OD): 7.33 (m,5), 5.10 (s,2), 4.13 (m,2), 2.86 (m,2), 2.65 (m,5), 1.90 (m,2), 1.65 (m,2), 1.23 (m,2); MS: m/z=292(M+1).

g. 4-(2-Oxo-tetrahydropyrimidin-1-yl)piperidine-1-carboxylic acid benzyl ester. A stirred solution of the above diamine (10.1 g) and 1,1'-carbonyldiimidazole (6.2 g) in chloroform (250 mL) was heated at reflux for 2 hours. The mixture was washed with water, and the separated organic phase was dried, evaporated, and chromatographed, with dichloromethane:methanol (90:10) as eluent. The pyrimidine was obtained as a white solid (7.4 g); NMR (CDCl$_3$): 7.35 (m,5), 5.12 (s,2), 4.75 (m,1), 4.50 (m,1), 4.26 (m,2), 3.27 (m,2), 3.13 (m,2), 1.89 (m,2), 1.63 (m,4); MS: m/z=318(M+1).

h. 4-(2-Oxoperhydropyrimidin-1-yl)piperidine. A solution of the piperidine (3.0 g) and 20% palladium hydroxide on carbon (0.410 g) in ethanol (100 mL) was stirred for 3.5 hours under 1 atmosphere of hydrogen. The reaction mixture was filtered through diatomaceous earth and the filtrate was evaporated to give the pyrimidone (1.6 g) as a white solid; NMR (CD$_3$OD): 4.25 (m,1), 3.22 (m,4), 3.08 (m,2), 2.63 (m,2), 1.87 (m,2), 1.60 (m,4); MS: m/z=184(M+1).

EXAMPLE 4

N-[1-[3-(3,4-Dichlorophenyl)-4-(2-phenyl-1,3,4-triazol-1-yl)butyl]-4-phenylpiperidin-4-yl]acetamide.

Using the procedure similar to that of Example 3, but replacing 1-(piperidin-4-yl)tetrahydropyrimidin-2-one with N-(4-phenylpiperidin-4-yl)acetamide, the title compound is obtained as a white solid; NMR (CD$_3$OD): 9.53 (s,1), 7.74 (m,1), 7.62 (m,2), 7.43–7.25 (m,8), 7.18 (d,1, J=2.1), 6.90 (dd,1, J=2.1, 8.3), 4.84 (dd,1, J=4.6, 14.2), 4.65 (dd,1, J=10.3, 14.2), 3.50 (m,2), 3.19 (m,4), 2.82 (m,1), 2.73 (m,2), 2.30 (m,4), 2.01 (s,3); MS: m/z=562(M+1). Analysis for C$_{31}$H$_{33}$Cl$_2$N$_5$O.3.00 HCl.0.20 Et$_2$O: Calculated: C, 55.61; H; 5.57; N, 10.19; Found: C, 55.66; H, 5.76; N, 10.13.

The intermediate piperidine was prepared as follows:

a. 4-Hydroxy-4-phenyl-1-trifluoroacetylpiperidine. To a suspension of 4-hydroxy-4-phenylpiperidine (20 g) in dichloromethane (100 mL) was added ethyl trifluoroacetate (14.8 mL). Acetonitrile (50 mL) was added as a co-solvent, and the solution was stirred overnight. The mixture was washed (aqueous sodium bicarbonate), and the separated organic phase was dried and evaporated to give the title compound as a yellow solid; the crude product was used in the next step without purification; MS: m/z=274(M+1).

b. 4-Azido-4-phenyl-1-trifluoroacetylpiperidine. To a suspension of sodium azide (9.5 g) in chloroform (100 mL) and trifluoroacetic acid (115 mL) cooled to 0° C. was added the above piperidine (20 g) in chloroform (100 mL) dropwise over a period of 1 hour. The mixture was allowed to warm to ambient temperature gradually and stirred overnight. After evaporating the chloroform and trifluoroacetic acid, the resulting mixture was diluted with aqueous sodium bicarbonate and extracted with dichloromethane. The organic extracts were dried and evaporated to give the azido piperidine as a viscous oil (20 g); NMR (CDCl$_3$): 7.41 (m,5), 4.51 (m,1), 3.97 (m,1), 3.61 (m,1), 3.26 (m,1), 2.10 (m,4); the crude product was used in the next step without purification; MS: m/z=299(M+1).

c. 4-Amino-4-phenyl-1-trifluoroacetylpiperidine and N-[4-Phenyl-1-(2,2,2-trifluoroacetyl)piperidin-4-yl]acetamide. A solution of the above azide (15 g) and 20% palladium hydroxide on carbon (1.5 g) in ethanol (150 mL) was stirred overnight under 1 barr of hydrogen. The reaction mixture was filtered through diatomaceous earth and the filtrate was concentrated in vacuo. The resulting oil was dissolved in dichloromethane and extracted with dilute aqueous hydrochloric acid. The acidic aqueous phase was extracted two times with dichloromethane (discarded), neutralized with saturated aqueous sodium bicarbonate, and extracted with dichloromethane. The organic extracts were dried and evaporated to give the intermediate amine; NMR (CD$_3$OD): 7.34 (m,5), 3.17 (m,1), 3.04 (m,1), 2.64 (m,1), 2.15 (m,1). To the amine in dichloromethane (80 mL) was added acetic anhydride (1.6 mL) and triethylamine (2.5 mL). After being stirred overnight, the mixture was washed successively with dilute hydrochloric acid and dilute aqueous sodium bicarbonate. The separated organic phase was dried and evaporated to give the acetamide as a white solid (13.0 g); NMR (CDCl$_3$): 7.30 (m,5), 6.08 (s,1), 4.24 (m,1), 3.82 (m,1), 3.48 (m,1), 3.23 (m,1), 2.65 (m,1), 2.42 (m,1), 2.09 (m,2), 2.00 (s,3); the crude product was used in the next step without purification; MS: m/z=315(M+1).

d. N-(4-Phenylpiperidin-4-yl)acetamide. To a solution of the above piperidine (13.0 g) in methanol (120 mL) was added lithium hydroxide monohydrate (5.2 g) in water (30 mL). After being stirred for 3 hours, the mixture was evaporated, diluted with water, and extracted with dichloromethane. The aqueous layer was saturated with sodium chloride and extracted with ethyl acetate. The combined organic extracts were dried and evaporated to give the deprotected acetamide as a white solid (2.5 g) by precipitation from acetonitrile; NMR (CD$_3$OD): 7.29 (m,5), 2.98 (m,4), 2.44 (m,2), 1.97 (m,5); NMR (CD$_3$OD/CF$_3$COOH): 7.31 (m,5), 3.28 (m,4), 2.68 (m,2), 2.18 (m,2), 2.02 (s,3); MS: m/z=219(M+1).

EXAMPLE 5

1-[3-(3,4-Dichlorophenyl)-4-(5-phenylimidazol-1-yl)butyl]-4-hydroxy-4-phenylpiperidine.

3-(3,4-Dichlorophenyl)-4-(5-phenylimidazol-1-yl) butyraldehyde (0.570 g) in methanol (3 mL) was added to a solution of 4-hydroxy-4-phenylpiperidine (0.422 mg) and acetic acid (0.14 mL) in methanol (4 mL). After 2 minutes, sodium cyanoborohydride (0.150 g) in methanol (3 mL) was added in a single portion. After being stirred overnight, the reaction mixture was diluted with aqueous sodium bicarbonate, stirred for 30 minutes, and extracted with dichloromethane. The organic extracts were dried, evaporated, and chromatographed, with dichloromethane:methanol (gradient 95:5, 90:10) as eluent, to give the title compound (0.550 g) as a white solid; NMR (CDCl$_3$): 7.49 (m,2), 7.38 (m,5), 7.25 (m,5), 6.94 (m,2), 6.67 (dd,1, J=2.1, 8.3), 4.25 (dd,1, J=6.2, 14.1), 4.08 (dd,1, J=8.8, 14.1), 2.81 (m,1), 2.59 (m,2), 2.36 (m,2), 2.08 (m,5), 1.72 (m,2); MS: m/z=520(M+1). Analysis for C$_{30}$H$_{31}$Cl$_2$N$_3$O.0.25CH$_2$Cl$_2$: Calculated: C, 67.07; H, 5.86; N, 7.75; Found: C, 66.88; H, 5.93; N, 7.78.

The intermediate aldehyde was prepared as follows:

a. 4-Amino-3-(3,4-dichlorophenyl)butan-1-ol. To a mechanically stirred solution of 2-(3,4-dichlorophenyl)-4-(tetrahydropyran-2-yloxy)butylamine (550 g) in methanol (3.3 L) was added in one portion 6.0N hydrochloric acid (352 mL) resulting in a slight exotherm. After being stirred for 3 hours, the reaction mixture was evaporated, and the resulting residue was diluted with water to 3 L volume. This solution was extracted with ether (2×500 mL), basified with sodium hydroxide pellets (100 g), and extracted with ethyl acetate (4×500 mL). The combined ethyl acetate extracts were washed (800 mL saturated sodium chloride), dried, and evaporated to give the alcohol as an amber oil (367 g) that solidified under high vacuum; NMR: 7.39 (d,1, J=8.2), 7.28 (d,1, J=2.0), 7.04 (dd,1, J=8.2, 2.0), 3.65 (m,1), 3.50 (m,1), 2.90 (m,2), 2.71 (m,1), 2.25 (m,2), 1.86 (m,2).

b. 3-(3,4-Dichlorophenyl)-4-(5-phenylimidazol-1-yl)butan-1-ol. The above amine (9.7 g) in methanol (37 mL) was added dropwise over a period of 15 minutes to a stirred solution of 1-isocyano-2-phenyl-1-tosylethene (11.8 g) in methanol (185 mL). After 30 minutes, triethylamine (5.8 mL) was added and the mixture was stirred overnight. The solvent was evaporated to give a residue that was dissolved in toluene and extracted with 1N hydrochloric acid. A viscous, dark-orange layer collected below the acidic aqueous phase which was separated, diluted with toluene, and extracted with 1N hydrochloric acid. The combined acidic aqueous extracts were basified with 10N sodium hydroxide and extracted with dichloromethane. The organic extracts were dried and evaporated to give a light orange solid that was dissolved in the minimum amount of refluxing dichloromethane. The addition of ether and hexane produced a precipitate that was collected by filtration and dried under vacuum to give the imidazolyl alcohol as an off-white solid (9.5 g); NMR (CD$_3$OD): 7.52 (d,1, J=1.1), 7.40 (m,3), 7.24 (m,3), 6.98 (d,1, J=2.1), 6.84 (d,1, J=1.1), 6.78 (dd,1, J=2.1, 8.3), 4.36 (dd,1, J=5.6, 14.2), 4.22 (dd,1, J=9.7, 14.2), 3.34 (m,1), 3.19 (m,1), 2.91 (m,1), 1.75 (m,2); MS: m/z=361 (M+1).

c. 3-(3,4-Dichlorophenyl)-4-(5-phenylimidazol-1-yl)butyraldehyde. To a solution of oxalyl chloride (0.60 mL) in dichloromethane (10 mL) at −78° C. was added methyl sulfoxide (0.98 mL) in dichloromethane (5 mL). After 10 minutes, the above alcohol (1.0 g) in dichloromethane (10 mL) was dropped in, and the mixture was stirred for 45 minutes. Triethylamine (3.86 mL) was then added and the solution was allowed to gradually warm to ambient temperature. The reaction mixture was diluted with dichloromethane, washed (1N hydrochloric acid, aqueous sodium bicarbonate, and water), dried, and evaporated. The crude product was chromatographed, with ether:dichloromethane:methanol (20:10:1) followed by dichloromethane:methanol (90:10) as eluent, to give the aldehyde as an off-white solid (0.610 g); NMR (CDCl$_3$/CF$_3$COOH): 9.58 (m,1), 8.74 (m,1), 7.56 (m,3), 7.27 (m,2), 7.20 (m,2), 6.87 (m,1), 6.69 (m,1), 4.56 (m,1), 4.35 (m,1), 3.42 (m,1), 2.90 (m,2); MS: m/z=359(M+1).

The intermediate isocyanide was prepared as follows:

d. N-(α-Tosylstyryl)formamide. Tosylmethyl isocyanide (73.4 g) in tetrahydrofuran (250 mL) was added dropwise to a stirred 1.0M solution of potassium tert-butoxide in tetrahydrofuran (500 mL) at −30° C. Benzaldehyde (38.2 mL) in tetrahydrofuran (150 mL) was then added dropwise at a temperature between −40° and −30° C. After being stirred for 1.5 hours, the mixture was poured into ice water, acidified by the dropwise addition of acetic acid (41.5 mL), stirred for 20 minutes, and neutralized with solid sodium bicarbonate. The tetrahydrofuran was removed in vacuo to give an aqueous solution with a light brown precipitate that was collected by filtration. The solid was dissolved in dichloromethane, washed with water, dried, and evaporated to give the crude product (101 g). This material was suspended in acetonitrile (400 mL) with stirring, dissolved by heating at reflux, and cooled to ambient temperature. After the dark red supernatant was decanted off, the precipitate was suspended in additional acetonitrile, filtered, and dried under vacuum to give the first crop of the formamide as a tan solid (56.6 g). The filtrate was concentrated and recrystallized using the same process to yield a second crop (18.7 g); NMR (CDCl$_3$): as a 1.7:1 mixture of olefin isomers: assignment 8.06 (CHO), 7.10 (NH), 2.43 (s, CH$_3$), 2.40 (s, CH$_3$); integration 8.06–7.09 (12), 2.43–2.40 (3); MS: m/z=302(M+1).

e. 1-Isocyano-2-phenyl-1-tosylethene. To a solution of the above formamide (2.0 g) in dichloromethane (26 mL) at −78° C. was added triethylamine (5.6 mL) and trifluoromethanesulfonic anhydride (1.7 mL). After being stirred for 1 hour, the reaction mixture was diluted with aqueous sodium bicarbonate and extracted with dichloromethane. The organic extracts were dried, evaporated, and chromatographed, with ether:hexane (1:1) as the eluent, to give the ethene as a viscous, light yellow oil (1.6 g); NMR (CD$_3$OD): 7.88 (m,5), 7.54 (m,5), 2.49 (s,3); MS: m/z=284(M+1).

Preparations 5b, 5d, and 5e were adaptations of literature procedures [van Leusen, A. M.; Schaart, F. J.; van Leusen, D. *Recl. Trav. Chim. Pays-Bas* 111, 517–523 (1992)].

EXAMPLE 6

1-[1-[(3S)-3-(3,4-Dichlorophenyl)-4-(5-phenyltetrazol-1-yl)butyl]-piperidin4-yl] tetrahydropyrimidin-2-one dihydrochloride.

(3S)-3-(3,4-dichlorophenyl)-4-(5-phenyltetrazol-1-yl)-butyraldehyde (0.90 g) in methanol (6 mL) and dichloromethane (2 mL) was added to a solution of 1-(piperidin-4-yl)tetrahydropyrimidin-2-one (0.458 g) and acetic acid (0.14 mL) in methanol (5 mL). After 40 minutes, sodium cyanoborohydride (0.157 g) in methanol (5 mL) was added in a single portion. After being stirred for 2 hours, the reaction mixture was diluted with aqueous sodium bicarbonate, stirred for 30 minutes, and extracted with dichloromethane. The organic extracts were dried, evaporated, and chromatographed, with dichloromethane:methanol (gradient 98:2, 70:30) as eluent. The purified material was dissolved in dichloromethane, precipitated out as the hydrochloride salt with ethereal hydrogen chloride, evaporated, and placed under high vacuum overnight to give the title compound as a white solid (0.928 g); NMR (CD$_3$OD): 7.61–7.47 (m,3), 7.30 (m,2), 7.21 (d,1, J=8.2), 7.03 (d,1, J=2.1), 6.75 (dd,1, J=2.1, 3.3), 4.94 (dd,1, J=4.8, 14.2), 4.74 (dd,1, J=9.4, 14.2), 4.34 (m,1), 3.58 (m,2), 3.25 (m,5), 3.15–2.98 (m,3), 2.76 (m,1), 2.33–2.11 (m,4), 1.90 (m,4); MS: m/z=528(M+1). Analysis for $C_{26}H_{31}Cl_2N_7O \cdot 0.15\ Et_2O \cdot 2.50\ HCl$: Calculated: C, 50.65; H, 5.59; N, 15.54; Found: C, 50.58; H, 5.61; N, 15.27.

The intermediate (3S)-3-(3,4-dichlorophenyl)-4-(5-phenyl-tetrazol-1-yl)-butyraldehyde was prepared as follows.

a. (3S)-4-Amino-3-(3,4-dichlorophenyl)butan-1-ol. To a mechanically stirred solution of D-tartaric acid (222 g) in methanol (4000 mL) at reflux was added 4-amino-3-(3,4-dichlorophenyl)butan-1-ol (342 g, from Example 5a) in warm methanol (2000 mL) in one portion and washed down with additional methanol (1000 mL). The mixture was heated to reflux. Crystals began to form before attaining the boiling point. After 1.5 hours at reflux, the solution was gradually cooled to room temperature, and stirred for 3 days. The tartrate salt was collected by suction filtration and dried in a vacuum oven at 60° C. to give product (232 g). This material was taken up in methanol (13.5 L) at boiling, and held at reflux for 1 hour allowing 1 L of methanol to distill off. The mixture was allowed to cool gradually to room temperature and stirred for 4 days. The first crop of crystals was collected by suction filtration and dried to give solid (178.8 g). The methanol filtrate was evaporated in vacuo to approximately 3 L volume. The resulting suspension was heated back to reflux to give a clear solution that was allowed to cool gradually to room temperature with stirring. A second crop of crystals (43.8 g) was collected. The combined crops of resolved amino-alcohol tartrates (222.6 g) were taken up in 1.0N sodium hydroxide (1.5 L) and extracted with dichloromethane (4×500 mL). The combined organic extracts were washed with brine, dried, and evaporated to give the chiral alcohol as an off white solid (135.4 g); melting point: 80°–82° C.; NMR (CD$_3$OD): 7.47 (d,1, J=8.3), 7.42 (d,1, J=2.1), 7.17 (dd,1, J=8.2, 2.1), 3.47 (m,1), 3.34 (m,1), 3.34 (m,1), 2.83 (m,3), 1.92 (m,1), 1.74 (m,1); MS: m/z=324(M+1).

b. N-[(2S)-2-(3,4-Dichlorophenyl)-4-hydroxybutyl]benzamide. Benzoic anhydride (14.6 g) in dichloromethane (50 mL) was added dropwise to a solution of (3S)-4-amino-3-(3,4-dichlorophenyl)butan-1-ol (15.0 g) and triethylamine (9.0 mL) in dichloromethane (200 mL) at 0° C. After being stirred at 0° C. for 1 hour and then at ambient temperature for 1 hour, the reaction mixture was washed (1N hydrochloric acid, saturated aqueous sodium bicarbonate) and the separated organic phase was dried and evaporated. The crude product was chromatographed, with dichloromethane:methanol (gradient 98:2, 90:10) to give the benzamide compound as a light yellow gum (17.5 g); NMR (CDCl$_3$): 7.65 (m,2), 7.48 (m,1), 7.38 (m,3), 7.33 (d,1, J=2.1), 7.07 (dd,1, J=2.1, 8.2), 6.44 (m,1,NH), 3.83 (m,1), 3.70 (m,1), 3.58–3.41 (m,2), 3.13 (m,1), 2.47 (m,1, OH), 1.99 (m,1), 1.84 (m,1); MS: m/z=338(M+1).

c. Acetic acid (3S)-4-benzoylarino-3-(3,4-dichlorophenyl)butyl ester. Acetyl chloride (4.6 mL) was added dropwise to a solution of acetic acid (3S)-4-benzoylamino-3-(3,4-dichlorophenyl)butyl ester (17.5 g) and pyridine (8.4 mL) in dichloromethane (400 mL) at 0° C. After being stirred overnight at room temperature, the reaction mixture was washed (water, saturated aqueous copper(II) sulfate), and the separated organic phase was dried and evaporated to give the ester compound as a light yellow oil. The crude product was used in the next step without purification (Spectral data same as Example 1f).

d. Acetic acid (3S)-3-(3,4-Dichlorophenyl)-4-(5-phenyltetrazol-1-yl)butyl ester. A solution of acetic acid (3S)-4-benzoylamino-3-(3,4-dichlorophenyl)butyl ester (7.0 g) in thionyl chloride (13.6 mL) was vigorously refluxed for 1 hour. The reaction mixture was diluted with toluene and evaporated. To the resulting residue in N,N-dimethylformamide (25 mL) cooled to 0° C. was added lithium azide (2.7 g) in N,N-dimethylformamide (35 mL). After being stirred for 1 hour, the mixture was diluted with dichloromethane and washed with copious amounts of water. The separated organic phase was dried, evaporated, and chromatographed, with dichloromethane:methanol (gradient 100:0, 90:10) as eluent, to give the terazolyl ester as a light yellow gum (5.0 g); NMR (CDCl$_3$): 7.58–7.45 (m,3), 7.24 (m,2), 7.17 (d,1, J=8.2), 6.85 (d,1, J=2.1), 6.59 (dd,1, J=2.1, 8.2), 4.73 (dd,1, J=5.5, 13.7), 4.50 (dd,1, J=9.4, 13.7), 4.04 (m,1), 3.81 (m,1), 3.36 (m,1), 2.12–1.89 (m,2), 1.99 (s,3); MS: m/z=405(M+1).

e. (3S)-3-(3,4-Dichlorophenyl)-4-(5-phenyltetrazol-1-yl)butan-1-ol. Using the procedure of Example 2c, replacing acetic acid 3-(3,4-Dichlorophenyl)-4-(2-phenylimidazol-1-yl)butyl ester by acetic acid (3S)-3-(3,4-Dichlorophenyl)-4-(5-phenyltetrazol-1-yl)butyl ester, the alcohol is obtained as a viscous oil that slowly crystallizes upon standing; NMR (CDCl$_3$): 7.58–7.45 (m,3), 7.26 (m,2), 7.15 (d,1,J=8.2), 6.87 (d,1, J=2.1), 6.62 (dd,1, J=2.1, 8.2), 4.79 (dd, 1, J=5.5, 13.8), 4.52 (dd,1, J=9.4, 13.8), 3.64 (m,1), 3.46 (m,2), 2.00 (m,1), 1.84 (m,1); MS: m/z=363(M+1).

f. (3S)-3-(3,4-Dichlorophenyl)-4-(5-phenyltetrazol-1-yl)-butyraldehyde. To a solution of oxalyl chloride (1.6 mL) in dichloromethane (44 mL) at −78° C. was added methyl sulfoxide (2.5 mL) in dichloromethane (22 mL). After 5 minutes, 3-(3,4-dichlorophenyl)-4-(5-phenyltetrazol-1-yl)butan-1-ol (4.3 g) in dichloromethane (22 mL) was dropped in, and the mixture was stirred for 25 minutes. Triethylamine (9.9 mL) was then added and the solution was allowed to gradually warm to ambient temperature. The reaction mixture was washed (1N hydrochloric acid, aqueous sodium bicarbonate, and water), and the separated organic phase was dried and evaporated. The crude product was chromatographed, with ether:dichloromethane (1:1) as eluent, and precipitated from ether to give the aldehyde as a white solid (2.7 g) (Spectral data same as Example 1h).

EXAMPLE 7

N-[1-[(3S)-3-(3,4-Dichlorophenyl)-4-(5-phenyltetrazol-1-yl)butyl]-4-phenyl-piperidin-4-yl]acetamide hydrochloride.

Using a procedure similar to that of Example 6, but using N-(4-phenylpiperidin-4-yl)acetamide, the title compound was obtained as a white solid; NMR (CD$_3$OD): 7.54 (m,3), 7.38–7.22 (m,8), 7.06 (d,1, J=2.1), 6.77 (dd,1, J=2.1, 8.3), 4.96 (dd,1, J=4.9, 14.2), 4.77 (dd,1, J=9.3, 14.1), 3.53 (m,2), 3.33–3.11 (m,4), 2.87 (m,1), 2.75 (m,2), 2.28 (m,4), 2.00 (m,3); MS: m/z=563(M+1). Analysis for $C_{30}H_{32}Cl_2N_6O \cdot 0.35\ Et_2O \cdot 1.80\ HCl$: Calculated: C, 57.57; H, 5.73; N, 12.82; Found: C, 57.33; H, 5.62; N, 12.61.

EXAMPLES 8–21

Using a procedure similar to that described in Example 6, except replacing the (3S)-3-(3,4-dichlorophenyl)-4-(5- phenyltetrazol-1-yl)butyraldehyde used therein, with (3S)-3-(3,4-dichlorophenyl)-4-(2-phenylimidalol-1-yl) butyraldehyde, and replacing the 1-(piperidin-4-yl) tetrahydropyrimidin-2-one used therein with the requsite piperidine, the following compounds of formula VII wherein $Q^1$ has the indicated value were prepared.

EXAMPLE 8

$Q^1$=4-(2-Oxoperhydropyrimidin-1-yl)piperidino; MS: m/z=526(M+1).

EXAMPLE 9

$Q^1$=4-Acetamido-4-phenylpiperidino; MS: m/z=561 (M+1).

EXAMPLE 10

$Q^1$=4-Ethoxycarbonyl-4-(2-oxopiperidino) piperidino; MS: m/z=597(M+1).

The intermediate piperidine for Example 10 was prepared as follows.

a. 8-Benzyl-1,3,8-triazaspiro[4.5]decane-2,4-dione. 1-Benzyl-4-piperidone (100 g) was added in a single portion to a mechanically stirred suspension of ammonium carbonate (488.5 g) and sodium cyanide (70.0 g) in water (700 mL) and ethanol (700 mL). The reaction mixture was stirred at 60° C. for 12 hours. The inorganic salts dissolve gradually in the solution and spirohydantoin crystals formed. Upon cooling to room temperature, the solids were collected by filtration, washed with warm water (2 L), recrystallized from 80% ethanol (2 L), washed with ethanol, and dried in a vacuum oven at 50° C. to give the hydantoin (122 g) as a white solid; MS: m/z=260(M+1); NMR (DMSO-d$_6$): 10.64 (bs,1), 8.45 (broad s,1), 7.29 (m,5), 3.48 (s,2), 2.69 (m,2), 2.28 (m,2), 1.81 (m,2), 1.51 (m,2).

b. 4-Amino-1-benzyl-4-carboxypiperidine. A stirred solution of the hydantoin (40.0 g) and lithium hydroxide monohydrate (32.4 g) in water (500 mL) was heated at reflux for 40 hours. The mixture was cooled to room temperature, filtered to remove the white precipitate, and the filtrate evaporated. The pH of the concentrate was adjusted from 12 to 5 with concentrated hydrochloric acid and the solution was evaporated to dryness. The residue was suspended in methanol to provide a white precipitate that was filtered, washed with methanol, and air-dried to give the amine (32.7 g) as a white solid; MS: m/z=235(M+1); NMR (DMSO-d$_6$): 7.40 (m,5), 3.89 (m,2), 2.92 (m,4), 2.12 (m,2), 1.84 (m,2).

c. 4-Amino-1-benzyl-4-ethoxycarbonylpiperidine. Thionyl chloride (43.0 mL) was added dropwise to a suspension of the amino-acid (23.0 g) in ethanol (400 mL) at 0° C. to give a clear solution. The reaction mixture was warmed to room temperature, refluxed for 5 hours, and stirred overnight at room temperature. The mixture was evaporated and stripped twice from toluene. The resulting oil was dissolved in water, adjusted to pH 3 with 1N sodium hydroxide, neutralized with saturated aqueous sodium bicarbonate, and extracted with dichloromethane. The organic extracts were dried and evaporated to give the ester (21.5 g) as an oil; MS: m/z=263(M+1); NMR: 7,28 (m,5), 4.17 (q,2, J=7.1), 3.52 (s,2), 2.50 (m,4), 2.13 (m,2), 1.54 (m,4), 1.27 (t,3, J=7.1).

d. 1-Benzyl-4-(5-chlorovaleramido)-4-ethoxycarbonylpiperidine. 5-Chlorovaleryl chloride (13.2 g) in dichloromethane (50 mL) was added dropwise to a solution of the above amino-ester (20.3 g) and pyridine (13.1 mL) in dichloromethane (250 mL) at 0° C., resulting in the formation of a thick slurry within 20 minutes. After being warmed to room temperature overnight, the slurry was diluted with aqueous sodium bicarbonate to give a clear, biphasic solution, which was further extracted with dichloromethane. The organic extracts were dried and evaporated to a light brown semi-solid. The material was suspended in ether and filtered to give the amide (16.8 g) as a white solid; MS: m/z=381(M+1); NMR (CD$_3$OD): 7.28 (m,5), 4.11 (q,2, J=7.1), 3.55 (m,4), 2.68 (m,2), 2.26 (m,4), 2.05 (m,4), 1.75 (m,4), 1.21 (t,3, J=7.1).

e. 1-Benzyl-4-ethoxycarbonyl-4-(2-oxopiperidino) piperidine. A solution of the above amide (16.8 g) in tetrahydrofuran (50 mL) was cannulated into a suspension of sodium hydride (2.1 g) in tetrahydrofuran (150 mL). After being stirred overnight, the reaction mixture was quenched with water, concentrated (to remove tetrahydrofuran), diluted with water, and extracted with dichloromethane. The combined organic extracts were dried and evaporated. The crude product was chromatographed, with dichloromethane:methanol (gradient 97:3, 95:5) as eluent, to give 1-benzyl-4-ethoxycarbonyl-4-(2-oxopiperidino)-piperidine (13.2 g) as a solid; MS: m/z=345(M+1); NMR (CD$_3$OD): 7.30 (m,5), 4.11 (q,2, J=7.1), 3.54 (s,2), 3.44 (m,2), 2.66 (m,2), 2.52 (m,2), 2.32 (m,2), 2.20 (m,2), 2.01 (m,2), 1.85 (m,2), 1.74 (m,2), 1.20 (t,3, J=7.1).

f. 4-Ethoxycarbonyl-4-(2-oxopiperidino)piperidine. A solution of 1-benzyl-4-ethoxycarbonyl-4-(2-oxopiperidino)piperidine (12.4 g) and 20% palladium hydroxide on carbon (2.0 g) in ethanol (150 mL) was stirred overnight under hydrogen (1 bar). The reaction mixture was filtered through diatomaceous earth, and the filtrate was evaporated to give 4-ethoxycarbonyl-4-(2-oxopiperidino)piperidine (9.1 g) as a viscous oil; MS: m/z=255(M+1); NMR (CD$_3$OD): 4.13 (q,2, J=7.1), 3.44 (m,2), 2.95 (m,4), 2.32 (m,2), 2.19 (m,2), 1.88 (m,4), 1.74 (m,2), 1.23 (t,3, J=7.1).

EXAMPLE 11

$Q^1$=4-Methoxycarbonyl-4-(2-oxopiperidino) piperidino; MS: m/z=583(M+1).

The intermediate piperidine for Example 11 was prepared as follows.

a. 1-Benzyloxycarbonyl-4-methoxycarbonyl-4-(2-oxopiperidino)-piperidine. (Trimethylsilyl) diazomethane (17.2 mL, 2.0M in hexanes) was added dropwise to a stirred suspension of 1-benzyloxycarbonyl-4-carboxy-4-(2-oxopiperidino) piperidine (4.0 g) in methanol (50 mL). After the solution became clear and the yellow color persisted, the reaction mixture was concentrated to an oil in vacuo. The crude product was chromatographed, with dichloromethane:methanol (95:5) as eluent, to give the title compound (4.0 g) as a white solid; MS: mz=375 (M+1); NMR (CD$_3$OD): 7.35 (m,5), 5.11 (s,2), 3.95 (m,2), 3.66 (s,3), 3.37 (m,2), 3.29 (m,2), 2.32 (m,2), 2.19 (m,2), 1.83 (m,4), 1.72 (m,2).

b. 4-Methoxycarbonyl-4-(2-oxopiperidino)piperidine. A solution of the compound from (a) and 20% palladium hydroxide on carbon in ethanol was stirred overnight under hydrogen. The mixture was filtered through diatomaceous earth and evaporated to give the piperidine;MS: m/z=241(M+1); NMR (CD$_3$OD): 3.66 (m,3), 3.44 (m,2), 2.93 (m,4), 2.32 (m,2), 2.17 (m,2), 1.86 (m,4), 1.74 (m,2).

EXAMPLE 12

Q$^1$=4-Methylaminocarbonyl-4-(2-oxopiperidino) piperidino; MS: m/z=582(M+1).

The intermediate piperidine for Example 12 was prepared as follows.
a. 1-Benzyloxycarbonyl-4-(methylaminocarbonyl)-4-(2-oxopiperidino)piperidine. A solution of 1-benzyloxy-4-carboxy-4-(2-oxopiperidino)piperidine, methylamine hydrochloride, 4-(dimethylamino)pyridine, triethylamine and 1-(3-dimethylaminopropyl)-3-ethylcarbodiimide hydrochloride in dichloromethane was stirred overnight. The mixture was diluted with dichloromethane and washed successively with 1.0N hydrochloric acid, saturated aqueous sodium bicarbonate, and water. The organic layer was dried and evaporated to give the amide; NMR: 7.35 (m,5), 6.72 (m,1), 5.12 (s,2), 3.56 (m,4), 3.30 (m,2), 2.78 (d, 3,J=4.8), 2.43 (m,2), 2.27 (m,2), 2.20 (m,2), 1.76 (m,4).
b. 4-(Methylaminocarbonyl)-4-(2-oxopiperidino) piperidine. A solution of the compound from (a) and 20% palladium hydroxide on carbon in ethanol was stirred overnight under hydrogen. The mixture was filtered through diatomaceous earth and evaporated to give the piperidine; MS: m/z=240(M+1); NMR (CD$_3$OD): 3.45 (m,2), 3.10 (m,2), 2.96 (m,2), 2.68 (m,3), 2.32 (m,2), 2.22 (m,2), 1.90 (m,4), 1.75 (m,2).

EXAMPLE 13

Q$^1$=4-(N,N-Dimethylaminocarbonyl)-4-(2-oxopiperidino)-piperidino; MS: m/z=596(M+1).

The intermediate piperidine for Example 13 was prepared as follows.
a. 1-Benzyloxycarbonyl-4-(dimethylaminocarbonyl)-4-(2-oxopiperidino)piperidine. A solution of 1-benzyloxycarbonyl-4-carboxy4-(2-oxopiperidino) piperidine, dimethylamine hydrochloride, 4-(dimethylamino)pyridine, triethylamine and 1-(3-dimethylaminopropyl)-3-ethylcarbodiimide hydrochloride in dichloromethane was stirred overnight. The mixture was diluted with dichloromethane and washed successively with 1.0N hydrochloric acid, saturated aqueous sodium bicarbonate, and water. The organic layer was dried and evaporated to give the amide; NMR: 7.35 (m,5), 6.72 (m,1), 5.12 (s,2), 3.56 (m,4), 3.30 (m,2), 2.78 (d,3, J=4.8), 2.43 (m,2), 2.27 (m,2), 2.20 (m,2), 1.76 (m,4).
b. 4-(Dimethylaminocarbonyl)-4-(2-oxopiperidino) piperidine. A solution of the compound from (a) and 20% palladium hydroxide on carbon in ethanol was stirred overnight under hydrogen. The mixture was filtered through diatomaceous earth and evaporated to give the piperidine; MS: m/z=254(M+1); NMR (CD$_3$OD): 3.45 (m,2), 3.09 (m,2), 2.92 (m,8), 2.38 (m,2), 2.26 (m,2), 1.92–1.69 (m,6).

EXAMPLE 14

Q$^1$=4-Aminocarbonyl-4-(piperidino)piperidino; MS: m/z=554(M+1).

The intermediate piperidine for Example 14 was prepared as follows.
a. 1-Benzyl-4-cyano-4-(piperidino)piperidine. Sodium cyanide (950 mg) was added to a solution of piperidine (1.65 g) in 1.0N hydrochloric acid (19.4 mL) at 0° C. 1-Benzyl-4-piperidone (3.7 g) in methanol (40 mL) was dropped in via an addition funnel, and the reaction mixture was allowed to warm to ambient temperature. After being stirred for 2.5 hours, a precipitate began to form and the reaction mixture was stirred overnight. The precipitate was filtered, washed with water, and dried under vacuum to provide the cyano compound (4.3 g) as a white solid; MS: m/z=284(M+1); NMR (CD$_3$OD): 7.28 (m,5), 3.54 (s,2), 2.90 (m,2), 2.59 (m,4), 2.25 (m,4), 1.73 (m,2), 1.62 (m,4), 1.49 (m,2).
b. 4-Aminocarbonyl-1-benzyl-4-(piperidino)piperidine. 1-Benzyl-4-cyano-4-piperidino-piperidine (3.7 g) was added portionwise with stirring to concentrated sulfuric acid (7 mL) at 0° C. The reaction mixture was placed into an oil bath preheated to 100° C., stirred for 1 hour, and poured into ice water. The aqueous solution was neutralized with 10N sodium hydroxide, adjusted to pH 11 with 1.0N sodium hydroxide, and extracted with dichloromethane. The organic extracts were dried and evaporated. The resulting solid was suspended in ether and filtered to give the title compound (3.1 g) as a white solid; MS: m/z=302(M+1); NMR (CD$_3$OD): 7.28 (m,5), 3.49 (s,2), 2.74 (m,2), 2.50 (m,4), 2.27 (m,2), 2.02 (m,2), 1.81 (m,2), 1.55 (m,4), 1.44 (m,2).
c. 4-Aminocarbonyl-4-(piperidino)piperidine. A solution of the compound from (b) (30 g) and 20% palladium hydroxide on carbon (4.0 g) in ethanol (250 mL) and tetrahydrofuran (90 mL) was stirred for 6 hours under 1 atmosphere of hydrogen. The reaction mixture was filtered through diatomaceous earth, and the filtrate was evaporated to give the title compound (21 g) as a white solid; MS: m/z=212(M+1); NMR (CD$_3$OD): 2.98 (m,2), 2.74 (m,2), 2.52 (m,4), 1.96 (m,2), 1.72 (m,2), 1.57 (m,4), 1.45 (m,2).

EXAMPLE 15

Q$^1$=4-(3-methyl-2-oxoperhydropyrimidin-1-yl) piperidino; MS: m/z=540(M+1).

The intermediate piperidine for Example 15 was prepared as follows.
a. 1-Benzyloxycarbonyl-4-(3-methyl-2-oxoperhydropyrimidin-1-yl)piperidine. Potassium tert-butoxide (19.3 mL, 1M in tetrahydrofuran) was added to a solution of 1-benzyloxycarbonyl-4-(2-oxoperhydropyrimidin-1-yl)piperidine (3.06 g) in tetrahydrofuran (88 mL). Iodomethane (2.4 mL) was then added, and the reaction mixture was stirred for 30 minutes. The reaction mixture was diluted with dichloromethane, washed with water, and chromatographed, with dichloromethane:methanol (gradient 98:2, 90:10) as eluent. The product was triturated from ether and filtered to give the N-methyl compound as a white solid (2.78 g); MS: m/z=332(M+1); NMR (CDCl$_3$): 7.34 (m,5), 5.12 (s,2), 4.53 (m,1), 4.26 (m,2), 3.21 (m,2), 3.11 (m,2), 2.93 (s,3), 2.86 (m,2), 1.91 (m,2), 1.60 (m,4).

b. 4-(3-Methyl-2-oxoperhydropyrimidin-1-yl)piperidine. The compound from (a) was hydrogenated under conditions similar to those described in Example 13 subpart (b) to give the piperidine; MS: m/z=198(M+1); NMR (CD$_3$OD): 4.19 (m,1), 3.14 (m,4), 2.98 (m,2), 2.80 (s,3), 2.53 (m,2), 1.82 (m,2), 1.48 (m,4).

EXAMPLE 16

Q$^1$=4-(3-ethyl-2-oxoperhydropyrimidin-1-yl) piperidino; MS: m/z=554(M+1).

The intermediate 4-(3-ethyl-2-oxoperhydropyrimidin-1-yl)-piperidine was prepared as follows.

a. 1-Benzyloxycarbonyl-4-(3-ethyl-2-oxoperhydropyrimidin-1-yl)-piperidine. Using the procedure of Example 15.a. except replacing iodomethane with iodoethane, the benzyloxycarbonyl compound was obtained as a white solid by trituration with ether; MS: m/z=346(M+1); NMR (CDCl$_3$): 7.34 (m,5), 5.12 (s,2), 4.54 (m,1), 4.26 (m,2), 3.38 (q,2, J=7.1), 3.22 (m,2), 3.11 (m,2), 2.86 (m,2), 1.90 (m,2), 1.60 (m,4), 1.10 (t,3, J=7.1).

b. 4-(3-Ethyl-2-oxoperhydropyrimidin-1-yl)piperidine. The compound from (a) was hydrogenated under conditions similar to those described in Example 13 subpart (b) to give the piperidine; MS: m/z=212(M+1); NMR (CDCl$_3$): 4.45 (m,1), 3.38 (q,2, J=7.1), 3.17 (m,6), 2.72 (m,2), 2.15 (m,1), 1.91 (m,2), 1.62 (m,4), 1.10 (t,2, J=7.1).

EXAMPLE 17

Q$^1$=4-Methyl-4-(2-oxopiperidino)piperidino; MS: m/z=525(M+1).

The intermediate piperidine for Example 17 was prepared as follows.

a. 1-Benzyl-4-hydroxy-4-methylpiperidine. 1-Benzyl-4-piperi-done (33.5 g) in tetrahydrofuran (500 ml) was added dropwise to a solution of methyllithium (100 mL, 1.4M in ether), methyllithium lithium bromide complex (93.0 mL, 1.5M in ether), and methyllithium lithium iodide complex (100 mL, 1.0M in ether) in tetrahydrofuran (170 mL). After being stirred for 3 hours, the reaction mixture was cooled in an ice bath, quenched with ethanol, and concentrated in vacuo. The resulting residue was dissolved in dichloromethane, washed with water, dried, and evaporated. The crude product was distilled to give the alcohol (34.4 g) as a colorless oil; bp 107°–140° C. (0.115 mm Hg); MS: m/z=206(M+1); NMR: 7.28 (m,5), 3.52 (s,2), 2.54 (m,2), 2.37 (m,2), 1.63 (m,4), 1.29 (bs,1), 1.24 (s,3).

b. 4-Acetamido-1-benzyl-4-methylpiperidine. Concentrated sulfuric acid (165 mL, 18M) was added dropwise to a solution of 1-benzyl-4-hydroxy4-methylpiperidine (33.9 g) in acetonitrile (190 mL). A white precipitate formed and slowly dissolved. After being stirred overnight, the reaction mixture was poured onto ice, adjusted to pH 10 with 3.0N sodium hydroxide, and extracted with dichloromethane. The organic extracts were dried and evaporated to give the amide as a white solid (33 g); MS: m/z=247(M+1); NMR: 7.29 (m,5), 5.15 (bs,1), 3.49 (s,2), 2.55 (m,2), 2.22 (m,2), 2.02 (m,2), 1.95 (s,3), 1.66 (m,2), 1.39 (s,3).

c. 4-Amino-1-benzyl-4-methylpiperidine. A solution of 4-acetamnido-1-benzyl-4-methylpiperidine (34.0 g) in concentrated hydrochloric acid (340 mL, 12.1N) was refluxed for 36 hours. The reaction mixture was cooled in an ice bath, and neutralized by the dropwise addition of concentrated sodium hydroxide (163 g in water). The solution was adjusted to pH 10 with additional aqueous sodium hydroxide, and extracted with dichloromethane. The organic extracts were dried and evaporated to give the amine as an amber oil (25.0 g); MS: m/z=205(M+1); NMR (CD$_3$OD): 7.28 (m,5), 3.52 (s,2), 2.45 (m,4), 1.54 (m,4), 1.10 (s,3).

d. 1-Benzyl-4-(5-chlorovaleramido)-4-methylpiperidine. 5-Chlorovaleryl chloride (4.2 mL) in dichloromethane (20 mL) was added to a solution of 4-amino-1-benzyl-4-methylpiperidine (6.0 g) and pyridine (5.0 ml) in dichloromethane (200 ml) at 0° C. After being stirred for 1 hour, the reaction mixture was washed with saturated aqueous copper(II) sulfate, dried, and evaporated. The crude product was chromatographed, with dichloromethane:methanol (gradient 98:2, 90:10) as eluent, to give the chloro compound as a white solid (2.4 g); MS: m/z=323(M+1); NMR (CD$_3$OD): 7.31 (m,5), 3.57 (m,2), 3.54 (s,2), 2.60 (m,2), 2.28 (m,2), 2.16 (m,4), 1.73 (m,4), 1.60 (m,2), 1.32 (s,3).

e. 1-Benzyl-4-methyl-4-(2-oxopiperidino)piperidine. 1-Benzyl-4-(5-chlorovaleramido)-4-methylpiperidine (2.1 g) in tetrahydrofuran (37 mL) was added to a suspension of sodium hydride (0.21 g) in tetrahydrofuran (5 mL). After being refluxed for 2 days, the reaction mixture was quenched with dilute aqueous hydrochloric acid, and evaporated.

The residue was dissolved in dichloromethane and washed with saturated aqueous sodium bicarbonate. The organic layer was dried and evaporated to give 1-benzyl-4-methyl-4-(2-oxo-piperidino)piperidine as a light orange oil (1.5 g); MS: m/z=287(M+1); NMR (CD$_3$OD): 7.30 (m,5), 3.51 (s,2), 3.30 (m,2), 2.50–2.29 (m,8), 1.87 (m,2), 1.72 (m,4), 1.33 (s,3).

f. 4-Methyl-4-(2-oxopiperidino)piperidine. Using the procedure of Example 1.o., replacing 1-benzyloxycarbonyl-4-(2-oxopiperidino)-4-(pyrrolidine-1-ylcarbonyl)piperidine with 1-benzyl-4-methyl-4-(2-oxopiperidino)piperidine, the piperidine was obtained as a white solid;
MS: m/z=197(M+1); NMR (CD$_3$OD): 3.33 (m,2), 2.78 (m,4), 2.36 (m,4), 1.79 (m,6), 1.36 (s,3).

EXAMPLE 18

Q$^1$=4-Methyl-4-(2-oxoperhydropyrimidin-1-yl) piperidino; MS: m/z=540(M+1).

The intermediate piperidine for Example 18 was prepared as follows.

a. 1-Benzyl-4-hydroxy-4-methylpiperidine. 1-Benzyl-4-piperi-done (33.5 g) in tetrahydrofuran (500 mL) was added dropwise to a solution of methyllithium (100 mL, 1.4M in ether), methyllithium lithium bromide complex (93.0 mL, 1.5M in ether), and methyllithium lithium iodide complex (100 mL, 1.0M in ether) in tetrahydrofuran (170 mL). After being stirred for 3 hours, the reaction mixture was cooled in an ice bath, quenched with ethanol, and concentrated in vacuo. The resulting residue was dissolved in dichloromethane, washed with water, dried, and evaporated. The crude product was distilled to give the alcohol (34.4 g) as a colorless oil; bp 107°–14° C. (0.115 mm Hg); MS: m/z=206(M+1); NMR: 7.28 (m,5), 3.52 (s,2), 2.54 (m,2), 2.37 (m,2), 1.63 (m,4), 1.29 (bs,1), 1.24 (s,3).

b. 4-Acetamido-1-benzyl-4-methylpiperidine. Concentrated sulfuric acid (165 mL, 18M) was added dropwise to a solution of 1-benzyl-4-hydroxy-4-methylpiperidine (33.9 g) in acetonitrile (190 mL). A white precipitate formed and slowly dissolved. After being stirred overnight, the reaction mixture was poured onto ice, adjusted to pH 10 with 3.0N sodium hydroxide, and extracted with dichloromethane. The organic extracts were dried and evaporated to give the amide as a white solid (33 g); MS: m/z=247(M+1); NMR: 7.29 (m,5), 5.15 (bs,1), 3.49 (s,2), 2.55 (m,2), 2.22 (m,2), 2.02 (m,2), 1.95 (s,3), 1.66 (m,2), 1.39 (s,3).

c. 4-Amino-1-benzyl-4-methylpiperidine. A solution of 4-acetamido-1-benzyl-4-methylpiperidine (34.0 g) in concentrated hydrochloric acid (340 mL, 12.1N) was refluxed for 36 hours. The reaction mixture was cooled in an ice bath, and neutralized by the dropwise addition of concentrated sodium hydroxide (163 g in water). The solution was adjusted to pH 10 with additional aqueous sodium hydroxide, and extracted with dichloromethane. The organic extracts were dried and evaporated to give the amine as an amber oil (25.0 g); MS: m/z=205(M+1); NMR (CD$_3$OD): 7.28 (m,5), 3.52 (s,2), 2.45 (m,4), 1.54 (m,4), 1.10 (s,3).

d. 1-Benzyl-4-[N'-(3-chloropropyl)ureido]-4-methylpiperidine. 3-Chloropropyl isocyanate (3.0 mL) in dichloromethane (20 mL) was added to a solution of 4-amino-1-benzyl-4-methylpiperidine (6.0 g) in dichloromethane (200 mL) at 0° C. After being stirred overnight, the reaction mixture was evaporated and the resulting material was dissolved in ether. A precipitate formed that was filtered off to give the chloro compound as a white solid (8.9 g); MS: m/z=324(M+1); NMR (CD$_3$OD): 7.32 (m,5), 3.59 (m,2), 3.56 (s,2), 3.21 (m,2), 2.61 (m,2), 2.35 (m,2), 2.04 (m,2), 1.89 (m,2), 1.60 (m,2), 1.32 (s,3).

e. 1-Benzyl-4-methyl-4-(2-oxoperhydropyrimidin-1-yl)piperidine. Potassium tert-butoxide (33.5 mL, 1.0M in tert-butanol) was added to a solution of 1-benzyl-4-[N'-(3-chloropropyl)ureido]-4-methylpiperi-dine (8.3 g) in tetrahydrofuran (62 mL). An additional equivalent of potassium tert-butoxide (25.8 mL, 1.0M in tert-butanol) was added, and the reaction mixture was stirred overnight. The reaction mixture was evaporated and the resulting residue was dissolved in water (pH 2). The acidic aqueous solution was extracted with dichloromethane (discarded), adjusted to pH 10 with 1.0 sodium hydroxide, and extracted with dichloromethane. The organic extracts were dried, evaporated, and dissolved in ether. A precipitate formed that was filtered off to give the 1-benzyl-4-methyl-4-(2-oxoperhydropyrimidin-1-yl)piperidine as a white solid (3.2 g); MS: m/z=288(M+1); NMR (CD$_3$OD): 7.30 (m,5), 3.51 (s,2), 3.23 (m,2), 3.15 (m,2), 2.50 (m,4), 2.34 (m,2), 1.82 (m,4), 1.29 (s,3).

f. 4-Methyl-4-(2-oxoperhydropyrirmidin-1-yl)piperidine. The compound from (e) was 15 hydrogenated under conditions similar to those described in Example 13 sub-part (b) to give the piperidine; MS: m/z=198(M+1); NMR (CD$_3$OD): 3.26 (m,2), 3.17 (m,2), 2.77 (m,4), 2.44 (m,2), 1.89 (m,2), 1.67 (m,2), 1.31 (s,3).

EXAMPLE 19

Q$^1$=4-(2-Oxo-2,3-dihydrobenzimidazol-1-yl)piperidino; MS: m/z=560(M+1).

EXAMPLE 20

Q$^1$=4-(2-Oxoperhydropyrimidin-1-yl)-4-(pyrrolidino-carbonyl)piperidino; MS: m/z=623(M+1).

The intermediate piperidine for Example 20 was prepared as follows.

a. 1-Benzyl-4-[N'-(3-chloropropyl)ureido]-4-ethoxycarbonyl-piperidine. 3-Chloropropyl isocyanate in dichloromethane (20 mL) was added to a solution of 4-amino-1-benzyl-4-ethoxycarbonylpiperidine (3.1 g) in dichloromethane (40 mL) at 0° C. After 10 minutes, the reaction mixture was evaporated, dissolved in ether to produce a precipitate, and filtered to give the title compound (3.5 g) as a white solid; NMR (CD$_3$OD): 7.31 (m,5), 4.12 (q,2, J=7.1), 3.58 (t,2, J=6.6), 3.53 (s,2), 3.21 (t,2, J=6.6), 2.69 (m,2), 2.32 (m,2), 2.11–1.85 (m,6), 1.22 (t,3, J=7.1).

b. 1-Benzyloxycarbonyl-4-[N'-(3-chloropropyl)ureido]-4-ethoxycarbonylpiperidine. 1-Chloroethyl chloroformate (2.83 mL) was added dropwise to a solution of 1-benzyl-4-[N'-(3-chloropropyl)-ureido]-4-ethoxycarbonylpiperidine (10 g) in 1,2-dichloroethane at 0° C. After 15 minutes, the reaction mixture was refluxed for 1 hour, evaporated, dissolved in methanol (200 mL), refluxed for 30 minutes, diluted with toluene, and evaporated. The crude residue was dissolved in dichloromethane (200 mL) followed by the addition of N-(benzyloxycarbonyloxy)succinimide (6.53 g) and triethylamine (7.3 ml). After 30 minutes, the reaction mixture was diluted with dichloromethane, and washed successively with 1.0N hydrochloric acid and dilute aqueous sodium bicarbonate. The separated organic phase was dried, evaporated, and purified by chromatography, with dichloromethane:ether (gradient 5:1, 1:1) as eluent, to give the title compound as a foamy, white solid (7.8 g); MS: m/z=426(M+1); NMR: 7.35 (m,5), 5.13 (s,2), 4.87 (m,2), 4.18 (q,2, J=7.1), 3.88 (m,2), 3.59 (m,2), 3.27 (m,4), 1.99 (m,6), 1.25 (t,3, J=7.1).

c. 1-Benzyloxycarbonyl-4-carboxy-4-[N'-(3-chloropropyl)ureido]-piperidine. A solution of 1-benzyloxycarbonyl-4-[N'-(3-chloropropyl)-ureido]-4-ethoxycarbonylpiperidine (7.6 g) in tetrahydrofuran (108 mL), methanol (35 mL), and 1.0N sodium hydroxide (36 mL) was stirred overnight. The reaction mixture was concentrated in vacuo, and the resulting basic aqueous solution was diluted with water and extracted with dichloromethane. The organic extracts were dried and evaporated to recover unreacted starting material (2.8 g). The aqueous layer was acidified with 1.0N hydrochloric acid, and extracted with dichloromethane. The organic extracts were dried and evaporated to give the title compound as foamy white solid (4.1 g); MS: m/z=380[(M+1-H$_2$O)]; NMR: 7.34 (m,5), 5.94 (m,2), 5.11 (m,2), 3.85 (m,2), 3.54 (m,2), 3.26 (m,4), 1.96 (m,6).

d. 1-Benzyloxycarbonyl-4-carboxy-4-(2-oxoperhydropyrimidin-1-yl)piperidine. Potassium tert-butoxide (25 mL, 1.0M in tert-butanol) was added to a solution of 1-benzyloxycarbonyl-4-carboxy-4-[N'-(3-chloropropyl)ureido]piperidine (3.9 g) in tetrahydrofuran (25 mL). After being stirred for 2 hours, the reaction mixture was evaporated, dissolved in water, and extracted with dichloromethane (discarded). The aqueous layer was acidified with 1.0N hydrochloric acid and extracted with dichloromethane. The organic extracts were dried and evaporated to a foamy solid which was suspended in ether and filtered to give the title compound as a white solid (3.2 g); MS: m/z=362(M+1); NMR: 7.35 (m,5), 6.58 (m,1), 5.12 (s,2), 3.70 (m,2), 3.53 (m,2), 3.34 (m,2), 3.26 (m,2), 2.27 (m,2), 1.95 (m,4).

e. 1-Benzyloxycarbonyl-4-(2-oxoperhydropyrimidin-1-yl)-4-(pyrrolidine-1-ylcarbonyl)piperidine. A solution of the compound from (d), pyrrolidine, 4-(dimethylamino)pyridine and 1-(3-dimethylaminopropyl)-3-ethylcarbodiimide hydrochloride in dichloromethane was stirred for 3.5 hours. The mixture was diluted with dichloromethane and washed successively with 1.0N hydrochloric acid, saturated aqueous sodium bicarbonate, and water. The organic layer was dried and evaporated to give the amide; NMR (CD$_3$OD): 7.35 (m,5), 5.11 (s,2), 3.96 (m,2), 3.38 (m,8), 3.17 (m,2), 2.28 (m,2), 1.91 (m,4), 1.79 (m,4).

f. 4-(2-Oxoperhydropyrimidin-1-yl)-4-(pyrrolidine-1-ylcarbonyl)piperidine. The compound from (e) was hydrogenated under conditions similar to those described in Example 13 sub-part (b) to give the piperidine; MS: m/z=281(M+1); NMR (CD$_3$OD): 3.41 (m,6), 3.16 (m,4), 2.98 (m,2), 2.28 (m,2), 2.00–1.78 (m,8).

EXAMPLE 21

$Q^1$=4-(5,5-Dimethyl-2-oxoperhydropyrimidin-1-yl)-piperidino; MS: m/z=554(M+1).

The intermediate 4-(2-oxo-5,5-dimethylperhydropyrimidin-1-yl)piperidine was prepared as follows.

a. 1-Benzyloxycarbonyl-4-(3-amino-2,2-dimethylpropylamino)-piperidine. 1-Benzyloxycarbonyl-4-oxopiperidine in methanol (72 mL) was added to a stirred solution of 2,2-dimethyl-1,3-propanediamine and acetic acid in methanol. After 15 minutes, sodium cyanoborohydride in methanol was added in a single portion. After being stirred overnight, the reaction mixture was evaporated; and the residue was dissolved in 1N hydrochloric acid. Concentrated hydrochloric acid was added dropwise and stirring was continued until the evolution of gas ceased. The acidic aqueous mixture was washed with dichloromethane, basified to pH 10 with 10N sodium hydroxide, and extracted with dichloromethane. The dichloromethane extracts were dried and evaporated to give the diamine; NMR (CD$_3$OD): 7.34 (m,5), 5.10 (s,2), 4.08 (m,2), 2.93 (m,2), 2.57 (m,1), 2.46 (s,2), 2.44 (s,2), 1.89 (m,2), 1.27 (m,2), 0.89 (s,6).

b. 1-Benzyloxycarbonyl-4-(2-oxo-5,5-dimethylperhydropyrimidin-1-yl)piperidine. A solution of the diamine (3.02 g) and 1,1'-carbonyldiimidazole (2.19 g) in chloroform (40 mL) was refluxed for 3 hours. The reaction mixture was diluted with dichloromethane and washed sequentially with 1N hydrochloric acid and aqueous sodium bicarbonate. The separated organic phase was dried, evaporated, triturated from ether, and filtered to give the urea as a white solid (1.72 g); MS: m/z=346(M+1); NMR (CD$_3$OD): 7.34 (m,5), 5.10 (s,2), 4.35 (m,1), 4.23 (m,2), 2.87 (m,6), 1.58 (m,4), 1.00 (s,6).

c. 4-(2-Oxo-5,5-dimethylperhydropyrimidin-1-yl)piperidine. The compound from (b) was hydrogenated under conditions similar to those described in Example 13 sub-part (b) to give the piperidine; MS: m/z=212 (M+1); NMR (CD$_3$OD): 4.28 (m,1), 3.10 (m,2), 2.92 (m,2), 2.89 (m,2), 2.66 (m,2), 1.59 (m,4), 1.03 (s,6).

FORMULAE

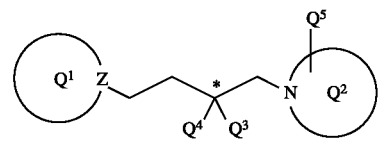
I

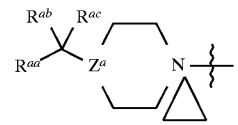
Ia

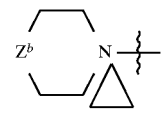
Ib

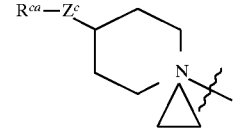
Ic

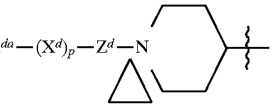
Id

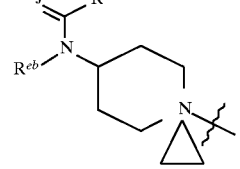
Ie

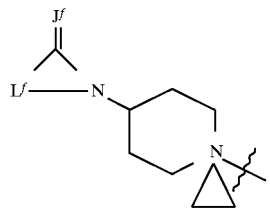
If

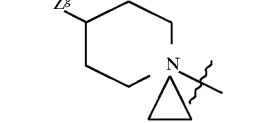
Ig

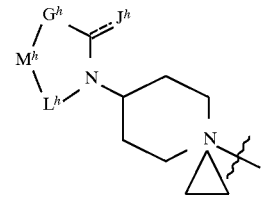
Ih

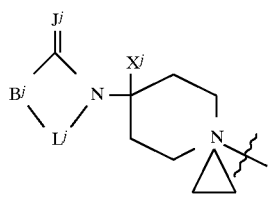
Ij

-continued
FORMULAE

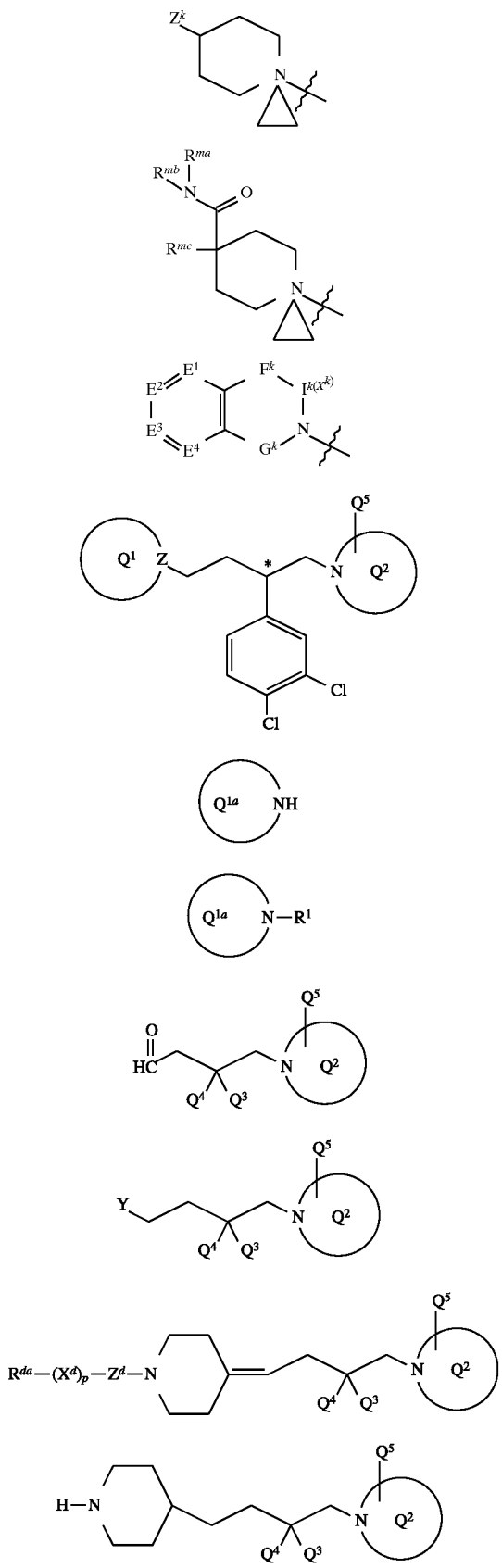

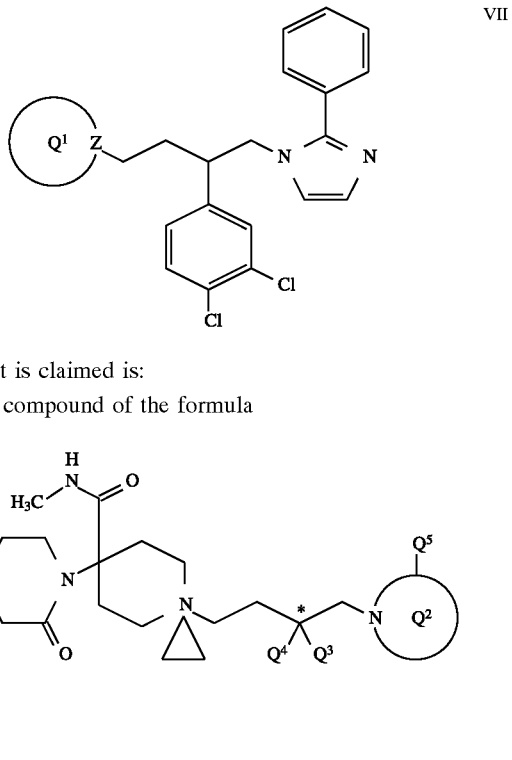

What is claimed is:

1. A compound of the formula

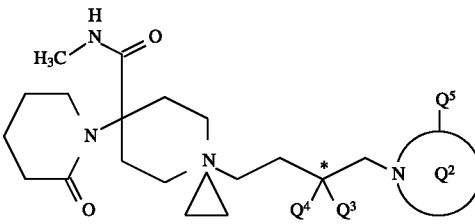

wherein $Q^2$ is a nitrogen-linked five-membered aromatic ring containing 1–4 nitrogens, which is substituted at a ring position adjacent to the nitrogen-link by a group $Q^5$;

$Q^3$ is hydrogen or (1–3C)alkyl;

$Q^4$ is phenyl which may optionally contain one or two substituents independently selected from halo, trifluoromethyl, hydroxy, (1–3C)alkoxy, (1–3C)alkyl and methylenedioxy; or $Q^4$ is thienyl, imidazolyl, benzothiophenyl or naphthyl any of which may optionally contain a halo substituent; or $Q^4$ is biphenylyl; or $Q^4$ is carbon-linked indolyl which may optionally contain a benzyl substituent at the 1-position; and $Q^5$ is selected from the group consisting of phenyl, benzyl, phenethyl and naphthyl, wherein any phenyl ring or naphthyl may optionally contain one or more substituents selected from (1–3C)alkyl, (1–3C)alkoxy, methylenedioxy, halogeno, hydroxy, (1–4C)acyloxy and $NR^AR^B$ in which $R^A$ and $R^B$ are independently hydrogen or (1–3C)alkyl, or $R^A$ is hydrogen or (1–3C) alkyl and $R^B$ is (1–4C)acyl;

or the N-oxide of a piperidino nitrogen indicated by Δ;

or a pharmaceutically acceptable salt thereof;

or a quaternary ammonium salt thereof in which the piperidino nitrogen indicated by Δ is a quadricovalent ammonium nitrogen wherein the fourth radical on the nitrogen is (1–4C)alkyl or benzyl and the associated counterion A is a pharmaceutically acceptable anion.

2. A compound according to claim 1 of the formula

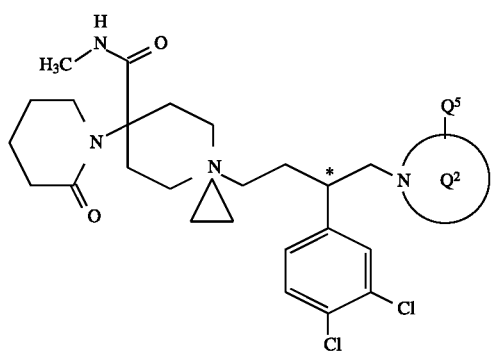

wherein Q² and Q5 have any of the meanings given in claim 1;
or the N-oxide of a piperidino nitrogen indicated by Δ;
or a pharmaceutically acceptable salt thereof;
or a quaternary ammonium salt thereof in which the piperidino nitrogen indicated by Δ is a quadricovalent ammonium nitrogen wherein the fourth radical on the nitrogen is (1–4C)alkyl or benzyl and the associated counterion A is a pharmaceutically acceptable anion.

3. A compound according to claim 1 wherein:
Q² is tetrazol-1-yl, or 1,3,4-triazol-1-yl;
Q³ is hydrogen; and
Q⁴ is 3,4-dichlorophenyl or 3,4-methylenedioxyphenyl;
or the N-oxide of a piperidino nitrogen indicated by Δ;
or a pharmaceutically acceptable salt thereof;
or a quaternary ammonium salt thereof in which the piperidino nitrogen indicated by Δ is a quadricovalent ammonium nitrogen wherein the fourth radical on the nitrogen is (1–4C)alkyl or benzyl and the associated counterion A is a pharmaceutically acceptable anion.

4. A compound according to claim 1 wherein:
Q² is imidazole-1-yl;
or the N-oxide of a piperidino nitrogen indicated by Δ;
or a pharmaceutically acceptable salt thereof;
or a quaternary ammonium salt thereof in which the piperidino nitrogen indicated by Δ is a quadricovalent ammonium nitrogen wherein the fourth radical on the nitrogen is (1–4C)alkyl or benzyl and the associated counterion A is a pharmaceutically acceptable anion.

5. A pharmaceutical composition which comprises a compound according to claim 1;
or the N-oxide of a piperidino nitrogen indicated by Δ;
or a pharmaceutically acceptable salt thereof;
or a quaternary ammonium salt thereof in which the piperidino nitrogen indicated by Δ is a quadricovalent ammonium nitrogen wherein the fourth radical on the nitrogen is (1–4C)alkyl or benzyl and the associated counterion A is a pharmaceutically acceptable anion;
and a pharmaceutically acceptable diluent or carrier.

6. A method of treating a disease in a human or other mammal in need thereof, in which NKA is implicated and antagonism of its action is desired, comprising: administering an effective amount of a compound according to claim 1;
or the N-oxide of a piperidino nitrogen indicated by Δ;
or a pharmaceutically acceptable salt thereof;
or a quaternary ammonium salt thereof in which the piperidino nitrogen indicated by A is a quadricovalent ammonium nitrogen wherein the fourth radical on the nitrogen is (1–4C)alkyl or benzyl and the associated counterion A is a pharmaceutically acceptable anion.

* * * * *